(12) United States Patent
Sprigle et al.

(10) Patent No.: US 8,095,706 B2
(45) Date of Patent: Jan. 10, 2012

(54) SYSTEMS AND METHODS FOR THE ANALYSIS OF MECHANICAL PROPERTIES OF MATERIALS

(75) Inventors: Stephen Sprigle, Marietta, GA (US); Linghua Kong, Marietta, GA (US); Qi Wang, Atlanta, GA (US); Vincent Hayward, Paris (FR); Jayme Caspall, Decatur, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 753 days.

(21) Appl. No.: 12/202,821

(22) Filed: Sep. 2, 2008

(65) Prior Publication Data
US 2009/0076732 A1 Mar. 19, 2009

Related U.S. Application Data

(60) Provisional application No. 60/970,340, filed on Sep. 6, 2007, provisional application No. 60/969,013, filed on Aug. 30, 2007.

(51) Int. Cl.
*G01L 1/16* (2006.01)

(52) U.S. Cl. .................................................... 710/42
(58) Field of Classification Search ..................... 702/42
See application file for complete search history.

(56) References Cited

U.S. PATENT DOCUMENTS

| | | | | |
|---|---|---|---|---|
| 5,426,979 | A * | 6/1995 | Kantorovich et al. | 73/628 |
| 5,862,803 | A * | 1/1999 | Besson et al. | 600/508 |
| 5,866,807 | A * | 2/1999 | Elings et al. | 73/105 |
| 7,530,945 | B2 * | 5/2009 | Rudischhauser et al. | 600/128 |
| 2005/0262944 | A1 * | 12/2005 | Bennett et al. | 73/592 |
| 2008/0262391 | A1 * | 10/2008 | Ottensmeyer | 600/587 |

* cited by examiner

*Primary Examiner* — Cindy H Khuu
(74) *Attorney, Agent, or Firm* — Bryan W. Bockhop; Bockhop & Associates, LLC

(57) ABSTRACT

The various embodiments of the present invention relate generally to the analysis of the mechanical properties of materials. More particularly, the various embodiments of the present invention relates to systems and methods of deriving the static and dynamic mechanical properties of deformative materials, for example, but not limited to, biological surfaces. The systems and methods of the present invention can be used to derive and evaluate the mechanical properties of many biological surfaces and subsurfaces, including but not limited to the skin.

16 Claims, 9 Drawing Sheets

SYSTEMS AND METHODS FOR THE ANALYSIS OF MECHANICAL PROPERTIES OF MATERIALS

RELATED APPLICATIONS

This application claims, under 35 U.S.C. §119(e), the benefit of U.S. Provisional Patent Application Ser. No. 60/970,340 filed 6 Sep. 2007 and U.S. Provisional Patent Application Ser. No. 60/969,013 filed 30 Aug. 2007, the entire contents and substance of which are hereby incorporated by reference as if fully set forth below.

TECHNICAL FIELD

The various embodiments of the present disclosure relate generally to the analysis of the mechanical properties of materials. More particularly, the various embodiments of the present invention relates to systems and methods of evaluating the static and dynamic, mechanical properties of deformable materials, for example, but not limited to, biological tissues.

BACKGROUND OF THE INVENTION

Pressure ulcers are widely considered to be a critical problem in rehabilitation because they result in severe discomfort and high healthcare costs. The prevention of pressure ulcers is a constant preoccupation for every nursing team as they are a significant secondary complication of mobility impairment. For example, more than 50% of individuals with a spinal cord injury (SCI) will develop a pressure ulcer during their lifetime, and the annual Medicare cost for pressure ulcers in the U.S. is approximately $1.3 billion, which accounts for 25% of the total health care cost for SCI. In addition, other skin diseases (e.g., chronic diseases) have supplanted communicable diseases as the leading cause of morbidity, mortality, and disability worldwide. In particular, venous diseases, such as lipodermatosclerosis, lymphedema, and scleroderma result in complex, non-healing, or recurring wounds accompanied by edema. Such conditions lead to prolonged periods of disability and significantly impact quality of life. Chronic leg wounds, such as pressure ulcers, in the U.S. are estimated to account for the loss of two million workdays a year. Furthermore, the annual cost for the management of these wounds exceeds $20 billion, which excludes the cost of lost workdays and productivity. As the U.S. population ages, the incidence of chronic wounds is expected to rise significantly with projected annual estimates of 5-7 million new cases of chronic wounds.

Early detection of chronic wounds and pressure ulcers is not always a simple matter. The prevalent preventative strategies for detection involve clinical inspection. Clinicians estimate disease stage and progression by feeling or palpating the skin. Palpation methods, however, do not provide an accurate measurement of disease stage and progression, are plagued by inherent subjectivity, and may vary significantly between clinicians, especially those with different levels of skill and experience. Other methods have been explored to objectively assess chronic wound and pressure ulcer risks. For example, a bioimpedance spectrometer was proposed to detect early pressure ulcers. Other approaches used color images to analyze the presence of skin erythema.

The detection of a stage I pressure ulcer is critical because the skin is still intact, and it is easier to recover from this condition. According to the National Pressure Ulcer Advisory Panel (NPUAP), a stage I pressure ulcer is defined as "an observable pressure related alteration of intact skin whose indicators as compared to an adjacent or opposite area on the body may include changes in one or more of the following: skin temperature (warmth or coolness), tissue consistency (firm or boggy feel) and/or sensation (pain, itching)." An important symptom of stage-I pressure ulcer is the change of tissue consistency. Since the skin and subcutaneous tissues start degrading on the early stage of the pressure ulcers, it is likely that the mechanical properties of the skin begin to change simultaneously. Based on past studies, it has been determined that measurement of the mechanical properties of the skin can be used to detect underlying skin diseases. The three main mechanical properties most relevant to clinical determination of pathological conditions are tissue stiffness, viscosity, and skin thickness.

Accordingly, there is a need for systems and methods that objectively measure the changes in the mechanical properties of the skin and the underlying tissue, which would provide an indirect and quantifiable measure of pathological changes in the skin. Much effort has already been dedicated to the development of devices for measuring the mechanical properties of human skin; however, presently available devices are large, expensive, cumbersome, involve complex loading patterns and boundary conditions, and require complex models and heavy data analysis, which are better suited for research studies as opposed to clinical practice. It is to the provision of low cost, handheld systems and methods for the objective, quantitative analysis of the mechanical properties of the skin, which provide a reliable measure across differences in time, environment, and user, that the various embodiments of the present invention are directed.

SUMMARY

Various embodiments of the present invention relate generally to the analysis of the mechanical properties of materials. More particularly, the various embodiments of the present invention relate to systems and methods of evaluating the static and dynamic, mechanical properties of deformable materials, for example, but not limited to, biological tissues. Broadly described, a system for deriving at least one mechanical property of a surface, the system comprising a dual-pinned flexion element adapted to derive at least one mechanical property of the surface. In an embodiment of the present invention, the dual-pinned flexion element can comprise a piezoelectric material. In embodiments of the present invention, the surface can be a biological surface or a biological subsurface, including but not limited to membranes, tissues, and organs of a human, an animal, a plant, or other living organisms, among others. In an exemplary embodiment, a tissue can comprise skin.

An aspect of the present invention comprises a system for deriving at least one property of a surface, the system comprising: at least two flexion elements adapted to contact the surface, at least two of the at least two flexion elements comprising a first flexion element and a second flexion element; at least two support members, wherein the first flexion element is attached to a first support member by a first pair of attachment elements, and wherein the second flexion element is attached to a second support member by a second pair of attachment elements; a drive system for driving at least two of the at least two flexion elements; a detection system to detect deflection of at least two of the at least two flexion elements; and a processing system to interpret the deflection of at least two of the at least two flexion elements detected by the detection system to derive at least one mechanical property of the surface. In an embodiment of the present invention, the first flexion element is positioned substantially parallel to the second flexion element in a non-driven state. In an embodiment of the present invention, at least two of the at least two flexion elements comprise a piezoelectric material. In an embodiment of the present invention, at least two of the at least two flexion elements are driven tangentially to the surface by the drive system. In another embodiment of the present invention, at least one flexion elements can be driven from a position not in contact with the surface to position in contact with the surface by the drive system.

An aspect of the present invention comprises a detection system. The detection system can comprise at least one strain gauge, which detects deflection of at least one of the at least two flexion elements. In an embodiment of the present invention, the detection system can comprise at least one sensor that contacts the surface.

An aspect of the present invention can further comprise a control system, wherein the control system controls the application of force to the surface. In an embodiment of the present invention, the control system can measure the application of force to the surface.

Various embodiments of a system for deriving the properties of a surface comprise deriving at least one mechanical property of the surface or subsurface, wherein the at least one mechanical property comprises elasticity, viscosity, surface stiffness, surface thickness, relaxation, creep, hysteresis, or combinations thereof. An aspect of the present invention comprises deriving at least one property of a surface, wherein the surface comprises a biological surface, such as the skin.

An aspect of the present invention comprises a method for deriving at least one property of a surface, the method comprising: contacting the surface with a dual-pinned flexion element; stimulating the surface by displacing the dual-pinned flexion element from an initial state to an driven state with a drive system; detecting the deflection of the dual-pinned flexion element by the surface; and deriving at least one mechanical property of the surface based upon the deflection of the dual-pinned flexion element. In an embodiment of the present invention, contacting a dual-pinned flexion element to a surface can comprise contacting a dual-pinned piezoelectric flexion element to a surface. In an embodiment of the present invention, contacting a dual-pinned flexion element to a surface can further comprise applying a desired force to the surface.

In an embodiment of the present invention, stimulating the surface with the dual-pinned flexion element can comprise driving the dual-pinned flexion element tangential to the surface by the drive system. In another embodiment of the present invention, stimulating the surface with the dual-pinned flexion element can comprise driving the dual-pinned flexion element with the drive system from a position not in contact with the surface to position in contact with the surface.

An aspect of the present invention comprises detecting the deflection of the dual-pinned flexion element by using a detection system comprising at least one strain gauge to a form a Wheatstone bridge. In an embodiment of the present invention, deriving at least one property of the surface comprises calculating elasticity, viscosity, surface stiffness, surface thickness, relaxation, creep, hysteresis, or combinations thereof. An aspect of the present invention can further comprise detecting the surface response to mechanical stimulation by contacting a sensor to the surface. An aspect of the present invention can further comprise controlling the application of force to the surface by the dual-pinned flexion element Other aspects and features of embodiments of the present invention will become apparent to those of ordinary skill in the art, upon reviewing the following description of specific, exemplary embodiments of the present invention in conjunction with the accompanying figures.

BRIEF DESCRIPTION OF DRAWINGS

Aspects of the disclosure can be better understood with reference to the attached drawings, described in greater detail below. The components in the drawings are not necessarily to scale, emphasis instead being placed upon clearly illustrating the principles of the present disclosure.

DETAILED DESCRIPTION

Figure 1:
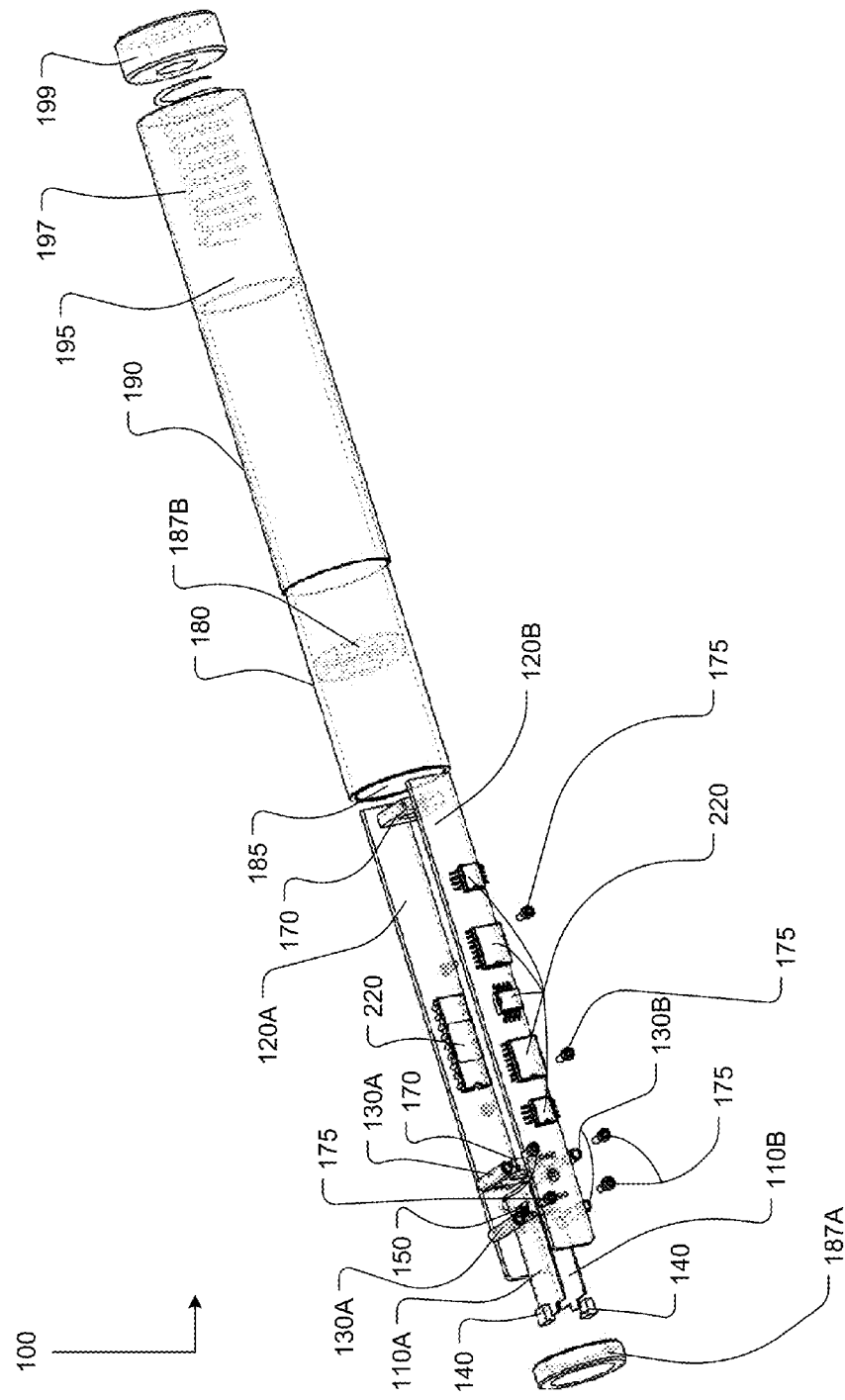
FIG. 1 is an exploded view of a system for contacting a surface.

The various embodiments of the present invention are directed to the analysis of the mechanical properties of materials. More particularly, the various embodiments of the present invention relates to systems and methods of evaluating the static and dynamic, mechanical properties of deformable materials, including but not limited to, their surfaces and subsurfaces. The systems and methods of the present invention can be used on many deformable surfaces and subsurfaces, including but not limited to, biological and non-biological surfaces and subsurfaces. Exemplary embodiments of biological surfaces and subsurfaces, include but are not limited to, membranes and tissues of a human, an animal, a plant, or other living organisms, among others. In an exemplary embodiment, a tissue can comprises skin, a dermal structure, a mucosal tissue, a membrane, or an organ, a muscle, among others.

As used herein, the terms "first," "second," and the like, "primary," "secondary," and the like, do not denote any order, quantity, or importance, but rather are used to distinguish one element from another. It must be noted that, as used in this specification and the appended claims, the singular forms "a," "an," and "the" include plural referents unless the context clearly dictates otherwise.

Systems and methods for the derivation of at least on mechanical property (e.g., stiffness and elasticity) of a biological surface (e.g., skin) can be used in the diagnosis of many pathological conditions. For example, changes in mechanical properties of the skin are known to accompany a number of chronic diseases and dysfunctions, such as lymphedema, chronic venous disease, scleroderma, pressure ulcers, and diabetes. The ability to monitor changes in the mechanical properties of biological surfaces can permit clinicians to diagnose pathological conditions, potentially in their early, more treatable stages.

Systems and methods for the derivation of at least one mechanical property of a biological surface allow for the objective measurement of disease staging and provide documentation of progression of the disease state or improvement over time. Similarly, systems and methods for the derivation of at least one mechanical property of biological surface can be utilized to assess the effectiveness of therapeutic interventions, such as pharmacological agents, strain reducing support surfaces, compression therapies, diabetic footwear, and skin adaptation strategies, among others. In the fields of orthotics and prosthetics, systems and methods for the derivation of at least one mechanical property of biological surface can facilitate the objective evaluation of different treatment approaches with regard to their relative effects on health and adaptation of biological tissues. For example, a patient's skin properties may help guide prosthetists in their choices between different socket designs (e.g., patellar tendon bearing versus total surface bearing) and interface techniques (e.g. hard sockets versus roll-on gel liners). Systems and methods for the derivation of at least one mechanical property of biological surface can also provide more calculated guidance for aspects of device design, such as the location and magnitude of corrective forces and load-bearing contours. Similarly, these objective measurements may be used as input data to CAD/CAM technologies, thereby adding further automation to custom device fabrication.

The various embodiments of the present invention provide improved systems, devices, and methods for evaluating the dynamic, mechanical properties of deformative materials. Embodiments of the present invention are capable of providing inexpensive, simple, compact, portable, light-weight, handheld devices capable of objective, quantitative analysis of at least one mechanical property of the skin. Embodiments of the present invention provide systems and methods that are consistent and reliable despite differences in time, environment, and user. There is a great need for this type of technology for a variety of applications, including but not limited to: medical diagnostics in the clinical setting, nursing homes, home health care, and in the field (for example, a rural or impoverished region); manufacturing; quality control; and the analysis for food products (e.g., analysis of butchery cuts, fish, poultry). The systems and methods of the present invention can provide a number of advantages including, but not limited to, low cost of manufacture, relative ease of operation, low operating and computing costs as a result of reduced data computation, the ability to manufacture the devices in small sizes, or the ability to incorporate the devices and its capabilities in a portable system.

The systems and methods of the present invention permit the detection of subtle changes in at least on mechanical property of a surface, such as the biomechanical properties of skin. An aspect of the systems and methods of the present invention comprise the ability to interrogate a localized area of a surface (e.g., a tissue) rather than averaging measurements over a larger area. Analysis of the localized are of a surface, such as the skin, permits the detection of localized necrosis or localized insults to the skin, such as incipient pressure ulcers, bruises, among others Embodiments of the present invention are inherently precise since there is no sliding surface and because it works in differential mode. The systems of the present invention also have a high bandwidth, which makes it possible to load the skin statically and dynamically under a wide range of conditions, such as in isotonic or in isometric conditions. By recording and analyzing the response of the skin, it is possible to rigorously monitor the biomechanical properties of the skin. Skin conditions such as stage I pressure ulcers, deep tissue injury and bruises can be reliably detected. The device is compact, light-weight, robust, and potentially low cost.

An aspect of the present invention comprises a system for deriving the properties of a surface, the system comprising: at least two flexion elements adapted to contact the surface, at least two of the at least two flexion elements comprising a first flexion element and a second flexion element; at least two support members, wherein the first flexion element is attached to a first support member by a first pair of attachment elements, and wherein the second flexion element is attached to a second support member by a second pair of attachment elements; a drive system for driving at least two of the at least two flexion elements; a detection system to detect deflection of at least two of the at least two flexion elements; and a processing system to interpret the deflection of at least two of the at least two flexion elements detected by the detection system to derive at least one mechanical property of the surface.

Referring now to the figures, wherein like reference numerals represent like parts throughout the several views, exemplary embodiments of the present invention will be described in detail. Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented.

The various embodiments of the present invention provide a system for contacting a surface 100 as illustrated in FIG. 1. The system 100 comprises at least two flexion elements 110A and 110B adapted to contact a surface, the at least two flexion elements 110A and 110B comprising a first flexion element 110A and a second flexion element 110B. The system can comprise two flexion elements 110A and 110B. In an embodiment of the present invention, the system 100 can comprise more than two flexion elements, such as three flexion elements or four flexion elements, or more. In an embodiment of the present invention, the system 100 can comprise at least two flexion elements 110A and 110B and at least one sensor element adapted to contact a surface or at least two sensors adapted to contact a surface. In such embodiments, the sensor element can comprise a piezoelectric material. In an embodiment of the present invention, the sensor element can be a flexion element.

Although an exemplary embodiment of the present invention comprises a system for contacting a surface 100, the system comprising at least two flexion elements 110A and 110B adapted to contact a surface, embodiments of the present invention can comprise systems and methods for contacting a surface, the system comprising at least one flexion element and a static element. The static element can comprise many stiff materials known in the art, including but not limited to metal, plastic, or ceramic. Thus, as described herein, the systems and methods of the present invention are applicable to the use of at least one flexion element and a static element or the use of at least two flexion elements.

In an exemplary embodiment of the present invention, the system 100 comprises at least two flexion elements 110A and 110B, wherein the first flexion element 110A is positioned substantially parallel to the second flexion element 110B in a non-driven state. The first flexion element 110A can be positioned about less than about ten (10) millimeters from the second flexion element 110B. The first flexion element 110A can be positioned about less than about five (5) millimeters from the second flexion element 110B. The first flexion element 110A can be positioned about less than about two (2) millimeters from the second flexion element 110B. In an exemplary embodiment of the present invention, the first flexion element 110A is positioned about one (1) millimeter from the second flexion element 110B.

The at least two flexion elements 110A and 110B can be made of many materials, including but not limited to piezoelectric materials. As used herein, the term "piezoelectric" is used to describe a material that mechanically deforms (changes shape) when a voltage potential is applied, or conversely, generates an electrical charge when mechanically deformed. Preferably, a piezoelectric material is disposed on strips of a flexible metal or ceramic sheet. The strips can be unimorph or bimorph. In an exemplary embodiment, the strips are bimorph, because bimorphs generally exhibit more displacement than unimorphs; however, unimorphs may be equally as effective.

One type of unimorph is a structure composed of a single piezoelectric element externally bonded to a flexible metal foil or strip. When a piezoelectric element is activated with a changing voltage, the element buckles or deflects as the strip opposes the movement of the piezoelectric element. The actuator movement for a unimorph can be by contraction or expansion. Unimorphs can only sustain low loads relative to the overall dimensions of the unimorph structure. In an embodiment of the present invention, the at least two flexion elements 110A and 110B each comprise a unimorph bender.

In contrast to the unimorph piezoelectric device, a bimorph device includes an intermediate flexible metal foil sandwiched between two piezoelectric elements. Bimorphs exhibit more displacement than unimorphs because under an applied voltage one ceramic element will contract while the other expands. Bimorphs can bend twice as much as a similar unimorph and generally cannot sustain high loads relative to the overall dimensions of the unimorph structure. In an exemplary embodiment of the present invention, the at least two flexion elements 110A and 110B each comprise a of bimorph bender.

Embodiments of the present invention contemplate that the size of a flexion element can vary depending upon the desired application. In an embodiment of the present invention, a bimorph bender can have a width of about 12 millimeters. In an exemplary embodiment of the present invention, a bimorph bender can have a width of about 12.7 millimeters.

Suitable piezoelectric materials include, but are not intended to be limited to, inorganic compounds, organic compounds, and metals. With regard to organic materials, all of the polymeric materials with non-centrosymmetric structure and large dipole moment group(s) on the main chain or on the side-chain, or on both chains within the molecules, can be used as suitable candidates for the piezoelectric film. Exemplary polymers include, for example, but are not limited to, poly(sodium 4-styrenesulfonate), poly (poly(vinylamine) backbone azo chromophore), and their derivatives; polyfluorocarbons, including polyvinylidenefluoride, its co-polymer vinylidene fluoride ("VDF"), co-trifluoroethylene, and their derivatives; polychlorocarbons, including poly(vinyl chloride), polyvinylidene chloride, and their derivatives; polyacrylonitriles, and their derivatives; polycarboxylic acids, including poly(methacrylic acid), and their derivatives; polyureas, and their derivatives; polyurethanes, and their derivatives; bio-molecules such as poly-L-lactic acids and their derivatives, and cell membrane proteins, as well as phosphate bio-molecules such as phosphodilipids; polyanilines and their derivatives, and all of the derivatives of tetramines; polyamides including aromatic polyamides and polyimides, including Kapton and polyetherimide, and their derivatives; all of the membrane polymers; poly(N-vinyl pyrrolidone) (PVP) homopolymer, and its derivatives, and random PVP-co-vinyl acetate copolymers; and all of the aromatic polymers with dipole moment groups in the main-chain or side-chains, or in both the main-chain and the side-chains, and mixtures thereof.

Piezoelectric material can also comprise metals such as lead, antimony, manganese, tantalum, zirconium, niobium, lanthanum, platinum, palladium, nickel, tungsten, aluminum, strontium, titanium, barium, calcium, chromium, silver, iron, silicon, copper, alloys comprising at least one of the foregoing metals, and oxides comprising at least one of the foregoing metals. Suitable metal oxides include $SiO_2$, $Al_2O_3$, $ZrO_2$, $TiO_2$, $SrTiO_3$, $PbTiO_3$, $BaTiO_3$, $FeO_3$, $Fe_3O_4$, $ZnO$, and mixtures thereof and Group VIA and IIB compounds, such as CdSe, CdS, GaAs, $AgCaSe_2$, ZnSe, GaP, InP, ZnS, and mixtures thereof. Preferably, the piezoelectric material is selected from the group consisting of polyvinylidene fluoride, lead zirconate titanate, and barium titanate, and mixtures thereof.

An aspect of the present system for contacting a surface 100 comprises at least two support members 120A and 120B, wherein the first flexion element 110A is attached to the first support member 120A by a first pair of attachment elements 130A, and the second flexion element 110B is attached to the second support member 120B by a second pair of attachment elements 130B. In an embodiment of the present invention, the at least two support members 120A and 120B can comprise many suitable insulative materials, including but not limited to a printed circuit board (PCB) or similar structures known in the art to mechanically support and electrically connect electronic components. A PCB is also commonly referred to as printed wiring board or an etched wiring board. The conductive layers of PCBS are typically made of thin copper foil. The insulating layers generally comprise a composite material of an epoxy resin, including but not limited to, FR-2, FR-3, FR-4, FR-5, FR-6, G-10, CEM-1, CEM-2, CEM-3, CEM-4, CEM-5. The at least two support members 120A and 120B can be separated and supported by a spacer element 170. In addition, the at least two flexion elements, 110A and 110B, can be separated and supported by a spacer element 170. The spacer element 170 can be attached to the support members, 120A and 120B, by many means know in the art, including but not limited to a screw 175.

In an embodiment of the present invention, the processing system 220 can be integrated on or in the at least two support members, 120A and 120B. In an embodiment of the present invention, the drive system 210 can be integrated on or in the at least two support members, 120A and 120B.

In an embodiment of the present invention, an attachment element can comprise many suitable attachment elements know in the art. In an exemplary embodiment of the present invention, an attachment element 130A and 130B comprises a pin. An aspect of the present invention comprises a dual-pinned bimorph bender. A bimorph bender mounted in a dual-pinned fashion structure is preferable to a cantilever structure in terms of stiffness and free deflection, as demonstrated by Wang and Hayward in *In vivo biomechanics of the fingerpad skin under local tangential traction* J. BIOMECH., 40 (2007) 851-860, which is hereby incorporated by reference in its entirety. Embodiments of the present invention contemplate that the distance between the attachment elements of a pair of attachment elements is variable. For example a pair of attachment elements (e.g., 130A and 130A or 130B and 130B) could be separated by a distance of about 7.5 mm, about 10 mm, about 12.5 mm, about 15 mm, or about 17.5 mm, among others. The distance between a pair of attachment elements can vary based upon the width and length of flexion element and the stiffness of material of interest, for instance, (e.g. skin). For example, the preferred distance between two pins is about 7.5 mm when the flexion elements are about 12.7 mm wide for analysis of human skin. Thus, systems and methods of the present invention permit "tuning" the deflection of the flexion elements. As used herein, the term "deflection" is used to describe the degree to which a structural element is displaced under a load.

The system for contacting a surface 100 comprises at least two flexion elements 110A and 110B adapted to contact a surface. In an embodiment of the present invention, at least two flexion elements apply a tangential force to the surface. Large surface strains can be achieved by pulling the surface from two traction surfaces moving in opposite directions. In an embodiment of the present invention, a flexion element may apply a force that is perpendicular to the surface. In an embodiment of the present invention, a flexion element may apply a force that is substantially perpendicular to the surface. In an embodiment of the present invention, at least one flexion elements can be driven from a position not in contact with the surface to position in contact with the surface by the drive system. Exertion of a force to "tap" the surface (i.e., from a position not in contact with the surface to position in contact with the surface) may permit interrogation of the surface and subsurface structures and features. In an embodiment of the present invention, at least two flexion elements apply a tangential force to the surface and at least one flexion element may apply a force that is non-tangential (e.g., perpendicular, substantially perpendicular, or the like) to the surface.

To eliminate the risk of electric shock, embodiments of the present invention can comprise an insulating element 140 to prevent direct contact between the target surface and a flexion element. The insulating element 140 can comprise many insulating materials suitable for the target surface (for example, biocompatible plastics for medical applications). In an exemplary embodiment of the present invention, the insulating element can comprise Delrin. The insulating element 140 can have a textured surface to increase traction and decrease slipping of the flexion element on the surface. In another embodiment of the present invention, the insulating element 140 can further comprise a traction element (e.g., a fine grit sand paper).

The at least two support members 120A and 120B, which respectively support the at least two flexion elements 110A and 110B via a first pair of attachment elements 130A and a second pair of attachment elements 130B can be inserted into a first housing 180 defining a first cavity 185. The first housing 180 can have a first capping member 187A and a second capping member 187B to enclose the first housing. In the use of the systems and methods of the present invention, a normal force component may be necessary to provide the friction grip necessary to load the skin in tension. To reduce the variance of the normal force exerted under manual application, the first housing 180 surrounds the flexion elements 110A and 110B in such a way as to limit the indentation deformation to a know distance (e.g., less than 1.5 mm).

In embodiments of the present invention, the system 100 can further comprise a second housing 190 defining a second cavity 195, wherein the first housing 180 is inserted into the second cavity 195 defined by the second housing. The second housing 190 can further comprise a spring 197 in physical communication with the first housing 180 and force transducer 199 to provide precise monitoring of the application force.

An aspect of the present invention can further comprise a control system, wherein the control system controls the application of force to the surface. In an embodiment of the present invention, the control system can measure the application of force to the surface, for example through a force sensor. In an embodiment of the present invention, the control system can control the application of force to the surface, for example through a constant force spring. The control system can measure and/or control the application of force to the surface by the system for contacting a surface 100. Thus, the system and methods of the present invention can measure and/or control the interface force between the system and the surface (e.g., tissue), and define the "seated" force of the system on the surface. In an embodiment of the present invention, the system can measure or control the deflection of the tissue at the interface in response to the normal loading of the system at the interface of the surface (in distinction to the deflection caused by the benders).

Figure 2:
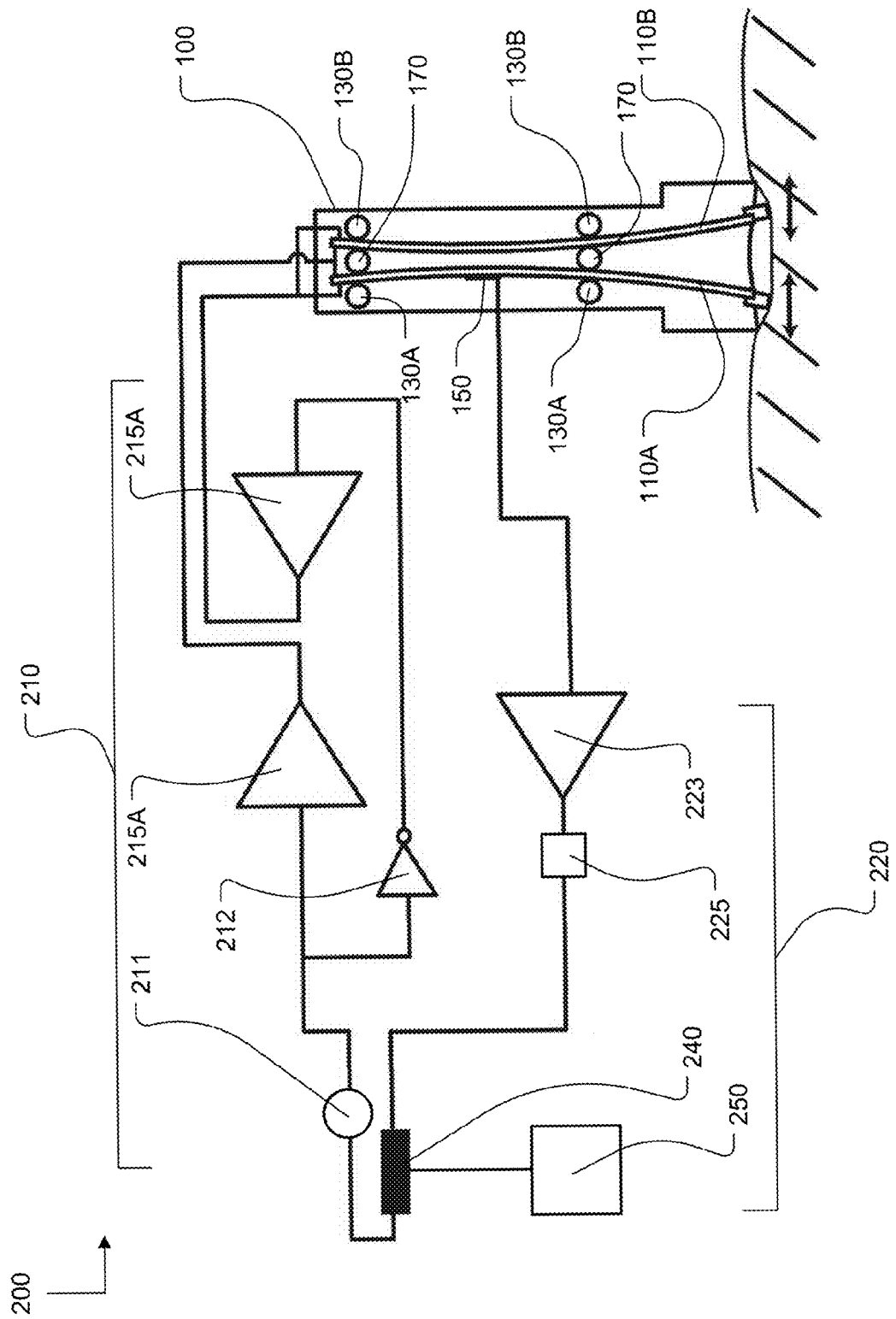
FIG. 2 is a schematic of a system for deriving the properties of a surface.

As illustrated in FIG. 2, a system for measuring at least one mechanical property of a deformative material 200 can comprise a system for contacting a surface 100. The system for measuring mechanical properties of deformative materials of the present invention comprises a drive system 210 for moving at least two flexion elements. The drive system 210 functions as a power source for driving or moving the flexion elements 110A and 10B. As such, a power source, a motor, or the like can be used to move the flexion elements. For example, rotational motion generated by a motor is converted to linear motion by a cam, a pulley, or the like to cause the flexion element. In embodiments of the present invention where the flexion element 110A and 10B comprises a piezoelectric material, the drive system 210 can comprise a power source 211 in electrical communication with at least two voltage amplifiers 215A and 215B. The voltage amplifiers can be high voltage amplifiers. In an embodiment of the present invention, the voltage amplifier can be integrated into the handheld unit. In an embodiment of the present invention, the voltage amplifiers 215A and 215B can be configured with an inverter 212 in an H-bridge circuit with the at least two flexion elements 110A and 110B, so that the potential difference between two electrodes varies from about −90V to about +90V. The voltage applied to the flexion elements can vary depending upon the composition of the flexion element (e.g. piezoelectric material) and the desired application. The electric energy supplied by the drive system 210 causes the flexion element to move, for example, tangentially to a surface. Thus, the flexion elements deflect in a controlled manner from an initial non-driven position to flexed driven state when a voltage is applied. In an embodiment of the present invention, the voltage applied can be about 45 V. In an embodiment of the present invention, the voltage applied can be less than 45 V.

In an embodiment of the present invention, the flexion elements 110A and 110B deflect simultaneously (i.e. analogous to a pair of tweezers in reverse) to apply a stress tangential to the target surface. The motion pattern of the flexion element 110A and 110B of the system can comprise an opening action of at least two flexion elements and a closing action of at least two flexion elements. In an exemplary embodiment of the present invention, a motion pattern is used in which a basic cycle comprises of opening action for increasing the distance between at least two flexion elements and a closing action for restoring the distance between the at least two flexion elements, and this motion is repeated. In an embodiment of the present invention, a pause can occur between the opening action and a closing action. Large skin strains can be achieved by pulling the skin from the at least two traction surfaces moving in opposite directions. The sensation created by the movement of the flexion elements is similar to a light vibration and causes no skin irritation.

The system for measuring at least one mechanical property of deformative material 200 of the present invention can also comprise a detection system to detect displacement of at least two flexion elements. In an embodiment of the present invention, the detection system 220 comprises at least one detection element. A detection element can comprise many devices capable of detecting a deformation or displacement, including but not limited to a strain gauge, an ultrasound transducer, a camera, a laser, a force transducer, an optical proximity sensor, an eddy current sensor, an acoustic wave sensor, or combinations thereof. In an embodiment of the present invention, the detection element can comprise at least one strain gauge 150. In an embodiment of the present invention, the detection system comprises at least one dual grid strain gauge. In an exemplary embodiment of the present invention, the detection system comprises two dual grid strain gages. The strain gauges can be associated with at least one flexion element. In an exemplary embodiment of the present invention, a dual grid strain gauge can be bonded to the side of each of at least two of the at least two flexion elements to form a Wheatstone bridge.

The detection system can detect a strain experienced by a target surface, which is caused by movement of at least two flexion elements 110A and 110B. The strain detected is transmitted to a processing system 220 as an electric signal. Thus, the known stress applied to the surface and the resulting strain indicated by the movement of the flexion elements depends on the mechanical properties of the target surface and or subsurface. From the numerical values of stress and strain, various mechanical properties of a target surface are calculated. Feedback modes can be used to increase the range and the measurement capabilities of the device. In an isotonic feedback mode, a regulation control loop can be applied to bend the flexion elements by a desired amount regardless of the surface deflection of the probed object, thus regulating the stress applied and measuring the resulting strain. In an isometric feedback mode, a regulation control loop can be applied to regulate the strain applied to a desired value. The stress needed to achieve the strain is also known. These modes can be better understood by considering the static equilibrium condition of the instrument loaded by an deformable object: $\delta = k_1 f + k_2 v$, where $\delta$ is the strain-causing deflection, $k_1$ is a factor that relates the stress-causing force, f, to the deflection $\delta$, and $k_2$ is a factor that relates the stress-causing voltage, v, to the deflection $\delta$. From this expression, it can be seen that the force, hence the stress, can be known from the applied voltage and the measured deflection, which is the manner to use the device in open loop mode. However, the closed loop modes can be used to increase the range of the measurement capabilities of the open loop device.

The system for measuring at least one mechanical property of a deformative material of the present invention can comprise a processing system 220 to interpret the displacement of at least two flexion elements 110A and 110B detected by the detection system to derive at least one mechanical property of the surface. The output (e.g., derived from the Wheatstone bridge) of the detection system can be processed a signal conditioning system. The signal conditioning system can comprise an instrumentation amplifier 223 and a low pass filter 225. In an exemplary embodiment of the present invention, the output of the detection system is processed by a low distortion instrumentation amplifier and a two-pole active low pass filter. In an embodiment of the present invention, the output of the detection system is passed through an about 100 Hz low pass filter. In an embodiment of the present invention, the output of the detection system is passed through an about 50 Hz low pass filter.

The processing system 220 can comprise a digital to analog converter (DAC) or an analog to digital converter (ADC) 240. The processing system 220 can comprises a processing unit 250. In an embodiment of the present invention, a personal computer can be used to interpret the displacement of at least two flexion elements 110A and 110B detected by the detection system to derive at least one mechanical property of the surface. In another embodiment of the present invention, the processing unit 250 to interpret the displacement of at least two flexion elements 110A and 110B detected by the detection system to derive at least one mechanical property of the surface can be integrated into the handheld device. Since computational capacity needed in the data processing is relatively low, a microprocessor/DSP could be used. Moreover, many commercially available general purpose microprocessors/DSPs have an integrated DAC and ADC. Therefore, the voltage amplifier, data processing, and human computer interface could be easily integrated to form a low cost, compact and robust mechanical parameter measuring system.

An aspect of the present invention comprises a method for deriving at least one property of a surface, the method comprising: contacting the surface with a dual-pinned flexion element; stimulating the surface by displacing the dual-pinned flexion element from an initial state to an open state with a drive system; detecting the deflection of the dual-pinned flexion element by the surface; and deriving at least one mechanical property of the surface based upon the deflection of the dual-pinned flexion element.

In an embodiment of the present invention, contacting a dual-pinned flexion element to a surface can comprise contacting a dual-pinned piezoelectric flexion element. In an embodiment of the present invention, contacting a dual-pinned flexion element to a surface can further comprise applying a desired force to the surface.

The system and methods of the present invention permit the detection of many mechanical properties, including but not limited to, elasticity, viscosity, surface stiffness, surface thickness, relaxation, creep, and hysteresis. The systems of the present invention have a high bandwidth to load the skin under a wide range of conditions, including statically, dynamically, quasi-statically, isotonically, and isometrically, among others. The systems and methods of the present invention permit the application of high strains to a surface. The systems and methods of the present invention permit the measuring of local biomechanical properties of the skin.

In an embodiment of the present invention, stimulating the surface with the dual-pinned flexion element can comprise driving the dual-pinned flexion element tangential to the surface by the drive system. In another embodiment of the present invention, stimulating the surface with the dual-pinned flexion element can comprise driving the dual-pinned flexion element with the drive system from a position not in contact with the surface to position in contact with the surface.

An aspect of the present invention comprises detecting the deflection of the dual-pinned flexion element by using a detection system comprising at least one strain gauge to a form a Wheatstone bridge. In an embodiment of the present invention, deriving at least one property of the surface comprises calculating elasticity, viscosity, surface stiffness surface thickness, relaxation, creep, hysteresis, or combinations thereof. An aspect of the present invention can further comprise detecting the surface response to mechanical stimulation by contacting a sensor to the surface.

An aspect of the present invention can further comprise a controlling the application of force to the surface. In an embodiment of the present invention, the controlling the application of force to the surface comprises monitoring, measuring, and controlling the application of force to the surface. Thus, the system and methods of the present invention can measure or control the interface force between the system and the surface (e.g., tissue), and define the "seated" force of the system on the surface. In an embodiment of the present invention, the methods of the present invention comprise measuring and/or controlling the deflection of the tissue at the interface in response to the normal loading of the system at the interface of the surface (in distinction to the deflection caused by the benders).

All patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention are provided herein, the present invention is not limited to these embodiments. There are numerous modifications or alterations that may suggest themselves to those skilled in the art.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Therefore, while embodiments of this invention have been described in detail with particular reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

EXAMPLES

Example 1

Experimental Evaluation of Skin

Materials and Methods. Two piezo bimorph benders (Model T220-H4-303Y; Piezo Systems Inc., Cambridge, Mass., USA) were mounted to form a pair of tweezers to tangentially stretch the skin as shown in FIGS. 1 and 2. To measure the relative displacement of the benders, two dual grid strain gages (Model EA-30-060PB350, Vishay Micro-Measurements, Raleigh, N.C., USA) were bonded on the both side of the benders, forming a Wheatstone bridge. The bridge output was processed by a low distortion instrumentation amplifier (Model INA1 03; Texas Instruments Inc., Dallas, Tex., USA) and filtered by a two-pole active low-pass filter (Model UAF42; Texas Instruments Inc., Dallas, Tex., USA) with cut-off frequency at 100 Hz. Two high voltage amplifiers (Model OPA445; Texas Instruments Inc., Dallas, Tex., USA) were configured in an H-bridge circuit to drive the piezo benders with potential difference between two electrodes varying from −90V to +90V. To eliminate risks of electric shock, two Delrin boots were glue on the tip of the piezoelectric benders. The Delrin boots were covered with a piece of sandpaper (120 Grit) to increase traction and prevent slipping. To stretch the skin tangentially, a normal force component is necessary. To reduce the variance of the normal force exerted under manual application, a plastic tube was used to guarantee a 1.5 mm indentation of the tweezer tip as shown in FIG. 2. The piezo bimorph bender is mounted in a dual-pinned structure. To make the device compact, two narrow rectangular printed circuit boards were used as the support for the hinge shafts. The strain gage signal conditioning circuit was laid on these two boards.

Figure 3:
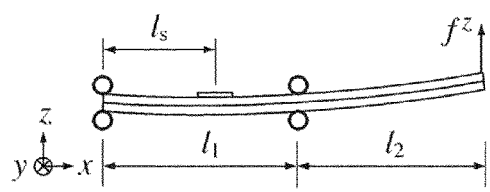
FIG. 3 is a schematic of a dual-pinned piezoelectric bimorph bending actuator.

Constituent equations. Referring to FIG. 3, the constituent equation of a dual-pinning installed bimorph piezo bender is given by:

$$\delta = \frac{(l_1+l_2)l_2^2}{2E\omega h^3}f^Z + \frac{3d_{31}(l_1+l_2)l_2}{4h^2}V \quad (1)$$

where $\delta$ is the deflection, $f^z$ is the external force applied at the tip of the bender, E is the piezo material's Young's modulus, h and $\omega$ are the thickness and width of the layers, $d_{31}$ is the piezoelectric coefficient, and V is applied voltage.

Since all governing equations of the bender are linear, at a certain applied voltage, the difference of strain at position $l_s$ is caused by the difference of the external load $f^z$. The bending moment at the position $l_s$ is:

$$M = \frac{l_s l_2}{l_1}f^Z \quad (2)$$

Therefore, the strain difference is found to be:

$$\epsilon_{diff} = \epsilon_{unload} - \epsilon_f^z = \frac{M}{EI} = \frac{3}{2}\frac{1}{wh^3 E}\frac{l_s l_2}{l_1}f^Z \quad (3)$$

where $I=8\omega h^3/12$ is the moment of inertia of the bender.

Calibration. To estimate deflection and external force accurately, Young's modulus E and the piezoelectric coefficient $d_{31}$ of the piezo material must be known. To calibrate these quantities, a dual pinned bender was vertically installed and a tiny mirror was glued at the tip to reflect a laser beam shining on. The deflection of the bender tip was gauged by measuring the displacement of the reflected beam using a lateral position sensing device (PSD, Model DL-10; UDT Sensors, Inc., Hawthorne, Calif., USA). The relation between the tip deflection and tip slope of a dual-pinning piezo bimorph bender could be derived as:

$$\theta = \frac{3}{2}\left(\frac{l_1}{2} + l_2\right)\frac{d_{31}V}{h^2} + \frac{1}{4}l_2(2l_1 + 3l_2)\frac{f^Z}{Ewh^3} \quad (4)$$

The coefficient $d_{31}$ was then calibrated by applying a quasi-static ramping voltage signal while recording the deflection. By applying a known load to the tip of the bender (15 g weight), the Young's modulus was obtained. To minimize errors, the experiments were conducted for $l_2$ equals to 7, 9, 11, 13, and 15 mm while total length $l_1+l_2$ is 30 mm. The results agreed to within 5%. The errors caused by actuator hysteresis were compensated by deriving the external force using the strain difference between the loaded and unloaded condition.

To verify that the device could reliably detect the disparity of biomechanical properties of skin, several experiments were conducted in which the elasticity and viscoelasticity of forearm skin and palm skin of human subjects were measured and compared. Previous work has shown that biomechanical properties of glabrous skin and hairy skin were quite different. Therefore, a clinically feasible device should be able to consistently distinguish these differences.

Subjects. Four healthy subjects, three males and one female, volunteered to participate.

Quasi-Static Stretch Protocol. A quasi-static ramp voltage varying from −90 V to +90 V was applied to the benders. In this case, the tweezers, formed by two benders, tangentially stretched the skin from an initial gap of 1 mm. The amplified strain gage signal was sampled at 2 kHz and stored in a personal computer. Before the experiment, the quasi-static ramp voltage was applied when the tweezers were unloaded. Then, the strain gage signal was recorded as a reference signal to evaluate skin resistive force according to equation 3. For each subject, four sites on both right forearm and right palm were randomly selected and tested.

Sinusoidal Loading Protocol. A 10 Hz sinusoid signal varying from −90 V to +90 V was applied to the benders. The amplified strain gage signal was sampled at 2 kHz and stored in a personal computer. To eliminate the artifacts caused by the hysteresis property of the piezoelectric material, the sinusoid voltage was applied before the experiment when the tweezers were unloaded, and the strain gage output was used as a reference signal in late data analysis. For each subject, four sites on both right forearm and right palm were randomly selected and tested.

Figure 4:
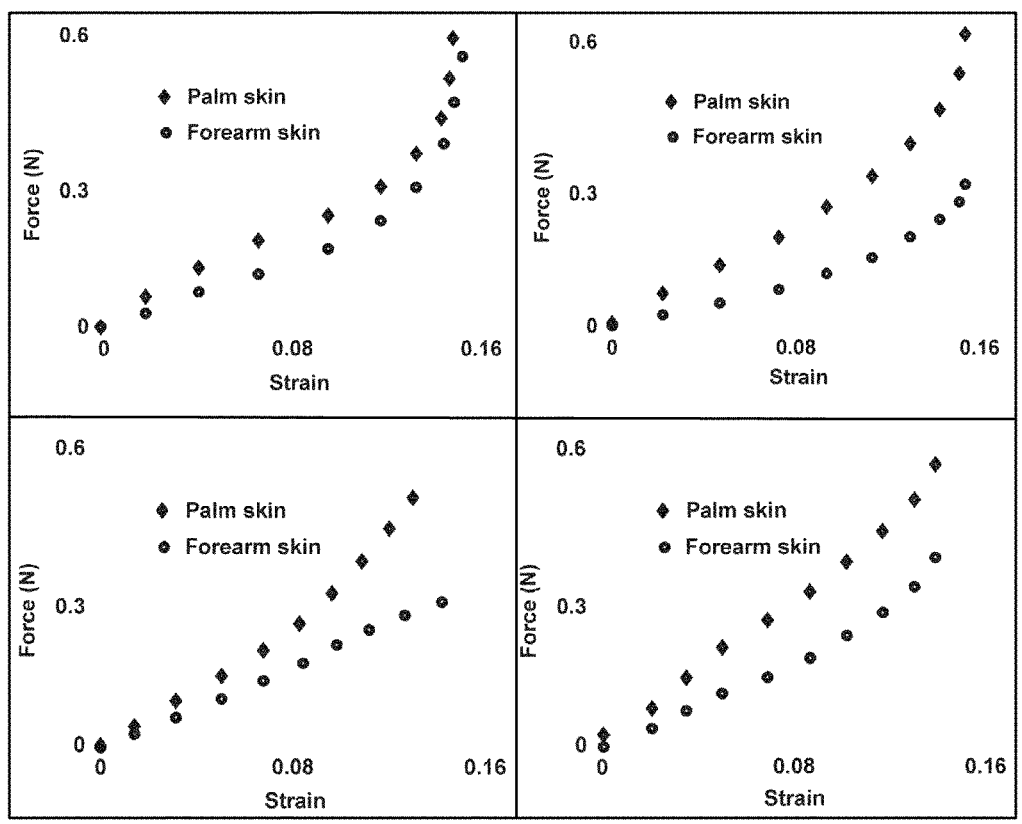
FIG. 4 are force-strain curves of palm skin and forearm skin of four subjects.

Results. The results of quasi-static stretch are seen in FIG. 4. From the measured force-strain relationship of the hairy skin, (i.e., the forearm skin), and glabrous skin, (i.e., palm skin), we could see that for some subjects, there were significant differences between the elasticity of the hairy skin and glabrous skin; for others, there were not. However, it is obvious that the hairy skin was consistently softer than the glabrous skin, which agrees with the literature of skin biomechanics.

Figure 5:
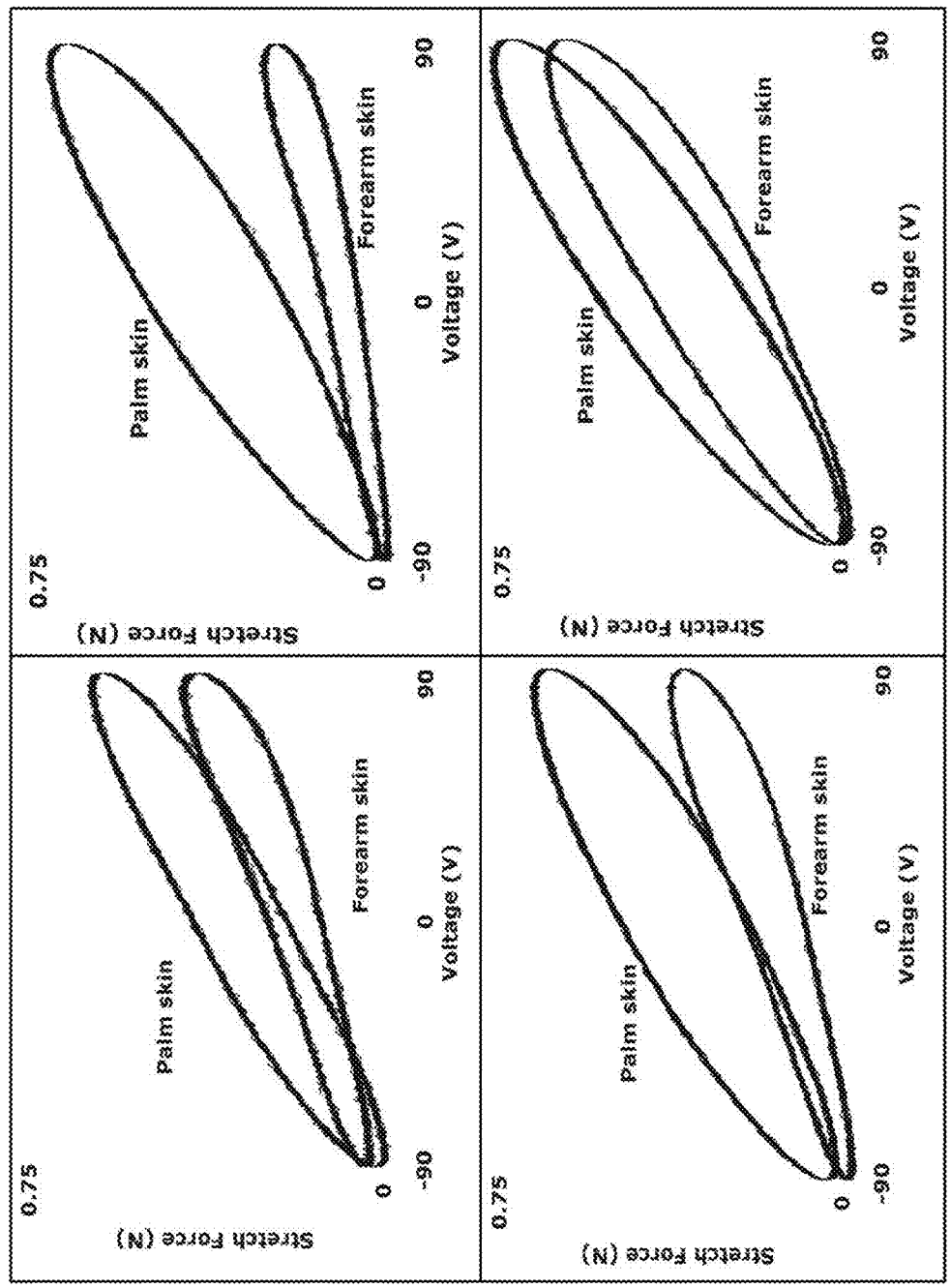
FIG. 5 illustrates the viscoelectric behavior of palm skin.

The skin responses to sinusoid signal are illustrated in FIG. 5. The phase difference between the input and output results from the viscoelastic properties of the skin. For each subject, the shape of the loop of the forearm skin and the palm skin was different, implying that there were substantial differences in the viscoelastic parameters. In each case, both the slope and the area under the curves could be used as indicators.

Example 2

Experimental Evaluation of Materials

The purpose of this Example was to perform a series of tests to evaluate the performance of a prototype measurement instrument referred to as the tissue interrogation device (TID). The TID was developed to serve as a point-of-care tool for clinicians and caretakers to objectively measure the mechanical properties of their patients' skin in vivo. The objectives of the present example were to characterize particular aspects of the prototype's reliability and validity. The results of these tests will help to increase understanding of the device's behavior and capabilities, as well as guide future device development, including design modifications and human subject protocols.

Methods. The skin interrogation device is a handheld instrument that utilizes a pair of piezoelectric bimorph benders that deflect in a controlled manner when voltage is applied. Like a pair of tweezers in reverse, the benders deflect simultaneously to apply a stress tangential to the skin's surface. To track the relative deflection of the benders for a given drive voltage, a pair of strain gages are mounted to each side of one of the benders, forming a Wheatstone bridge. The benders are capped by plastic feet that isolate the skin from the electronics and include a high-friction coating designed to prevent slippage between the benders and test surface. A load cell (Entran ELF-TC1000-10) was added in series with the device and instrumented to provide precise monitoring of the application force. A virtual instrument was created in the LabView computer program to provide the software interface for controlling the device operation (e.g., bender oscillation frequency, sampling rate, and collection period) and for displaying and recording test results.

For all bench tests, commercially available prosthetic liners were chosen as the test material. These liners are elastomeric interfaces used in the prosthetics field for individuals with limb amputations. They are worn directly against the skin to provide benefits such as load dampening and suspension. The decision to test liners was made because they have a wide range of known characteristics, they have properties that are generally similar to those of the skin, and because of bonus educational benefit for the student prosthetist. Twelve different types of liners were collected for testing, all of which have been characterized in detail by researchers. The liners vary by manufacturer, material composition, material thickness, fabric backing, and most importantly, their mechanical properties, including shear and tensile stiffness (see Table 1).

TABLE 1

| Manufacturer | Liner | Material Composition (Sanders et al. 2004) | Mean Sample Thickness (mm) | Current Test Sample Thickness (mm) |
| --- | --- | --- | --- | --- |
| ALPS | Alps Clearpro 3 mm | silicon elastomer | 2.1 | 3.2 |
|  | Alps ELDT 6 mm | silicone gel w/fabric backing | 5.6 | 5.9 |
|  | Alps Super Stretch | silicone gel | 6.1 | 6.5 |
| Engineered Silicone | ESP Aegis Ultimate | silicone gel w/fabric backing | 5.1 | 5.4 |

TABLE 1-continued

| Manufacturer | Liner | Material Composition (Sanders et al. 2004) | Mean Sample Thickness (mm) | Current Test Sample Thickness (mm) |
|---|---|---|---|---|
| Products | ESP Streamline | silicone elastomer | 2.2 | 2.0 |
| Ossur | Iceross Comfort Plus 6 mm | silicone elastomer w/fabric backing | 5.9 | 6.0 |
| | Iceross Dermo 6 mm | gel silicone w/fabric backing | 5.8 | 6.1 |
| | Iceross Original 2-color | silicone elastomer (2 layers) | 2.3 | 2.1 |
| | Iceross Original Clear | silicone elastomer | 3.4 | 3.3 |
| Otto Bock | Profile Urethane | urethane | 6.3 | 6.8 |
| Ohio Willow Wood | Alpha 9 mm | silicone gel w/fabric backing | 9.4 | 9.3 |
| Silipos | Siloliner | silicone gel w/fabric backing | 5.2 | 5.1 |

A test sample was cut from each liner, taking care to match the thicknesses to those studied by Sanders et al. Samples were cut as circumferential strips, each approximately 4.5 cm wide. Additionally, each sample was lightly cleaned prior to testing in order to remove any dust particles that could affect results.

Each liner sample was tested in a randomized order under loaded conditions in which the device feet were applied to the surface of the material. The device's bimorph benders were driven to oscillate at 1 Hz. Recall that there are number of procedural variables that have the potential to affect the device output. Therefore, a bench-top positioning device, or jig, was utilized to precisely control device orientation, application force, material deflection, and angle of approach. The liner samples were placed on the rigid platform of the jig in a consistent orientation relative to the bender feet, and various adjustments in the jig facilitated consistent application force (5 N) and approach angle (vertical). Additionally, the tests were conducted under mild ambient conditions to avoid any affects of extremes in temperature and humidity.

To facilitate statistical analyses, eight consecutive trial repetitions were collected for each liner. For analysis of the test results, the voltage responses from the strain gages (proportional to the bender deflections) were used to calculate an approximate stiffness value for the liners. To evaluate the TID's differentiating ability, one-way ANOVA between groups was used to determine whether any significant differences occurred in the approximated stiffness results for the 12 liners. Then Tukey's post-hoc tests were used for pair-wise comparison of all liners to determine where any significant differences occurred and the magnitude of their differences. For these tests, a significance level 0.05 and confidence intervals of 95% were utilized. To analyze the relationship between the TID results and the liners' reported mechanical properties, linear regression analysis was used including calculation of the coefficient of determination $R^2$. Here, the explanatory variables were the shear stiffness and tensile stiffness values reported by Sanders et al., and the response variable was the approximated stiffness results from the TID.

Results. The skin interrogation device's mean approximated stiffness results for each of the tested liners are provided in Table 2 along with the liners' shear and tensile stiffness properties.

TABLE 2

| | | | | Sanders et al. (2004) | | SID Project | | |
|---|---|---|---|---|---|---|---|---|
| Liner | | Material Composition | Fabric Backing | Shear Modulus (kPa) | Tension Modulus (kPa) | Sample Thickness (mm) | Approximate Stiffness | |
| | | | | | | | mean | st dev |
| Alps Clearpro | A | silicon elastomer | no | 90.54 | 131.39 | 3.2 | 1.7906 | 0.0324 |
| Alps ELDT 6 mm | B | silicone gel | yes | 23.28 | 76.09 | 5.9 | 0.2929 | 0.0062 |
| Alps Super Stretch | C | silicone gel | no | 21.19 | 30.41 | 6.5 | 0.3074 | 0.0033 |
| ESP Aegis Ultimate | D | silicone gel | yes | 43.99 | 87.88 | 5.4 | 0.3703 | 0.0183 |
| ESP Streamline | E | silicone elastomer | no | 175.2 | 205.01 | 2.0 | 2.0452 | 0.1244 |
| Iceross Comfort Plus | F | silicone elastomer | yes | 41.55 | 55.86 | 6.0 | 0.6084 | 0.0148 |
| Iceross Dermo 6 mm | G | gel silicone | yes | 52.86 | 56.28 | 6.1 | 1.0388 | 0.0355 |
| Iceross Original 2-color | H | silicone elastomer | no | 125.92 | 118.76 | 2.1 | 2.5449 | 0.1946 |

TABLE 2-continued

| Liner | Material Composition | Fabric Backing | Sanders et al. (2004) | | Sample Thickness (mm) | SID Project | |
|---|---|---|---|---|---|---|---|
| | | | Shear Modulus (kPa) | Tension Modulus (kPa) | | Approximate Stiffness mean | st dev |
| Iceross Original Clear | I silicone elastomer | no | 124.54 | 194.53 | 3.3 | 2.5481 | 0.1288 |
| Alpha 9 mm | J silicone gel | yes | 26.49 | 50.05 | 9.3 | 0.3449 | 0.0033 |
| Siloliner | K silicone gel | yes | 19.29 | 40.77 | 5.1 | 0.3291 | 0.0076 |
| Profile Urethane | L urethane | no | 82.73 | 88.06 | 6.8 | 1.2032 | 0.0312 |

Figure 6:
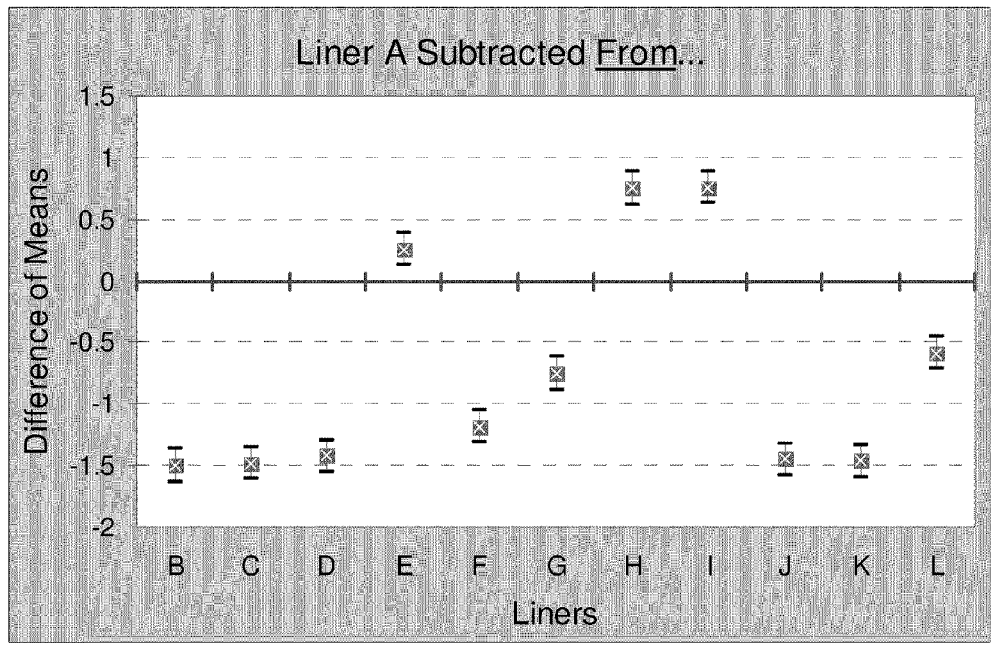
FIG. 6 graphically depicts the ability of the tissue interrogation device to differentiate materials.
Figure 7:
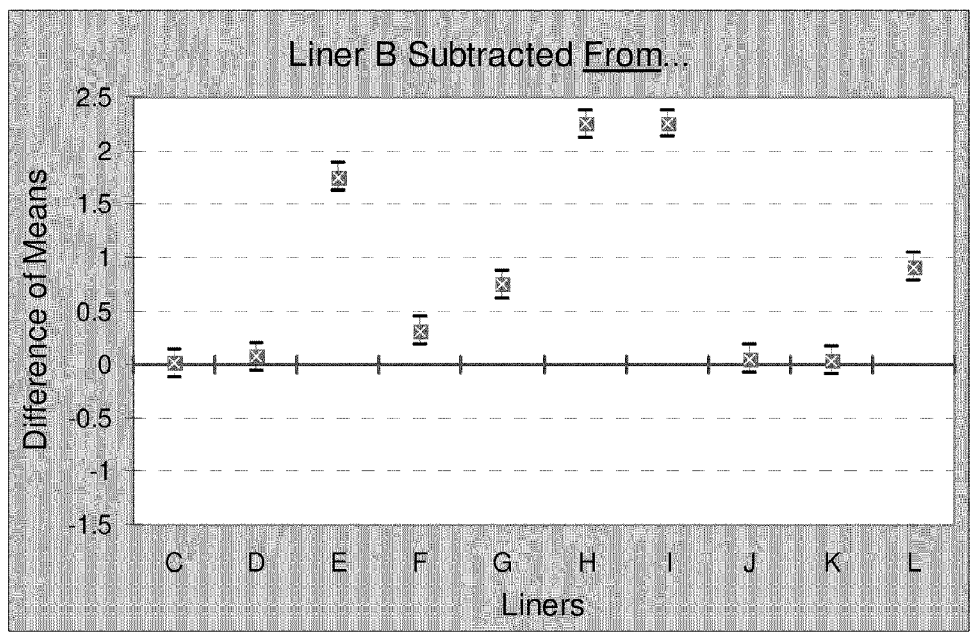
FIG. 7 graphically depicts the ability of the tissue interrogation device to differentiate materials.

To assess the ability of the TID to differentiate tested materials, the post-hoc analysis compared the prototype's results for each of the 12 liners with every other liner, leading to a total of 66 comparisons between pairs of liners. For each paired comparison, the analysis computed the difference in the mean results of the two liners and the statistical significance of this difference. FIG. 6 illustrates a first example of the results. Here, the mean result for liner A is subtracted from that of the other liners, which are listed along the x-axis. The y-axis shows the difference between each liner pair, and the vertical error bars indicate the 95% confidence intervals for each difference. For this example, none of the confidence intervals cross zero, so it appears that the TID was able to detect a significant difference between liner A and all the others. The graph also illustrates that liner A is softer than liners E, H, and I but stiffer than the others. FIG. 7 depicts a second example result, which shows that the TID successfully differentiated liner B as softer than six liners (E, F, G, H, I, and L). However, for the comparisons with C, D, J, and K, the confidence intervals include zero, illustrating that the TID was not successful in differentiating these pairs.

Figure 8:
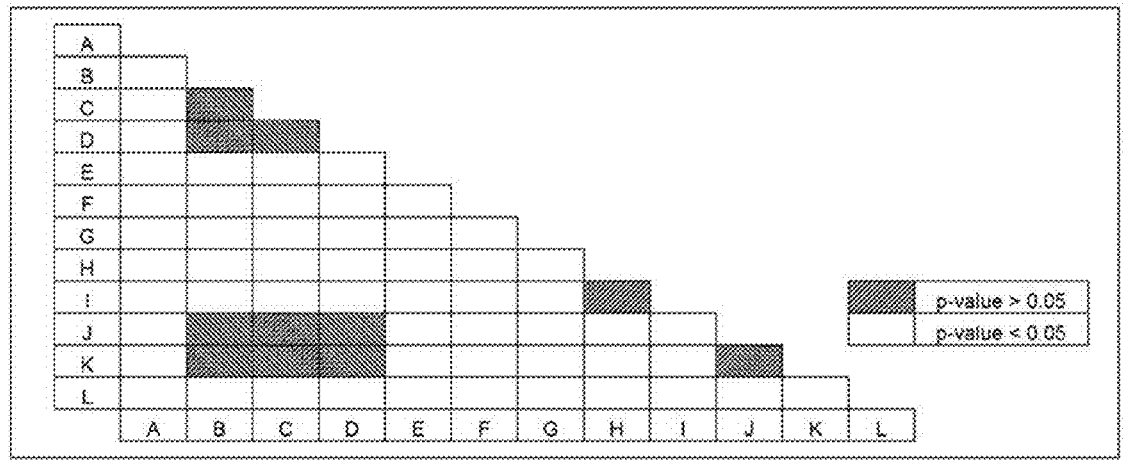
FIG. 8 is illustrates a comparison of the ability of the tissue interrogation device to differentiate materials.

FIG. 8 illustrates the results for all 66 liner comparisons. Overall, the TID was able to successfully differentiate 55 (83%) of the liner pairs. The device was not able to detect a significant difference between any of the liners B, C, D, J, or K, accounting for 10 of the undifferentiated pairs. Additionally, no significant difference was found for liners H and I.

Figure 9:
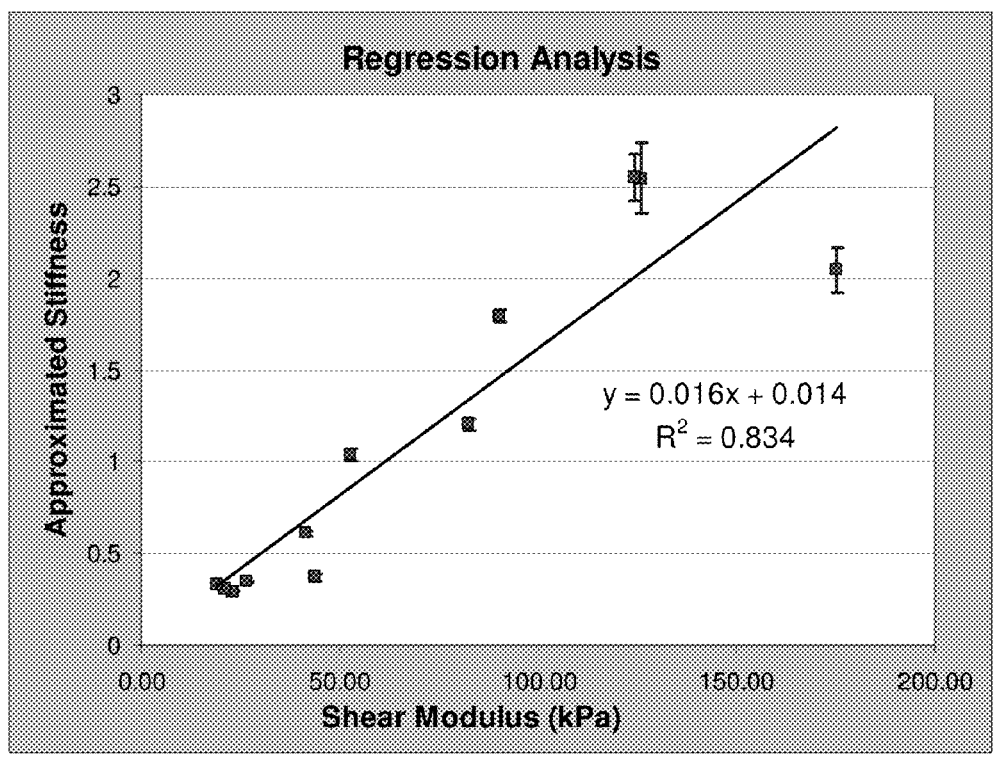
FIG. 9 graphically depicts the relationship between the stiffness findings of tissue interrogation device as compared to reported shear stiffness values.
Figure 10:
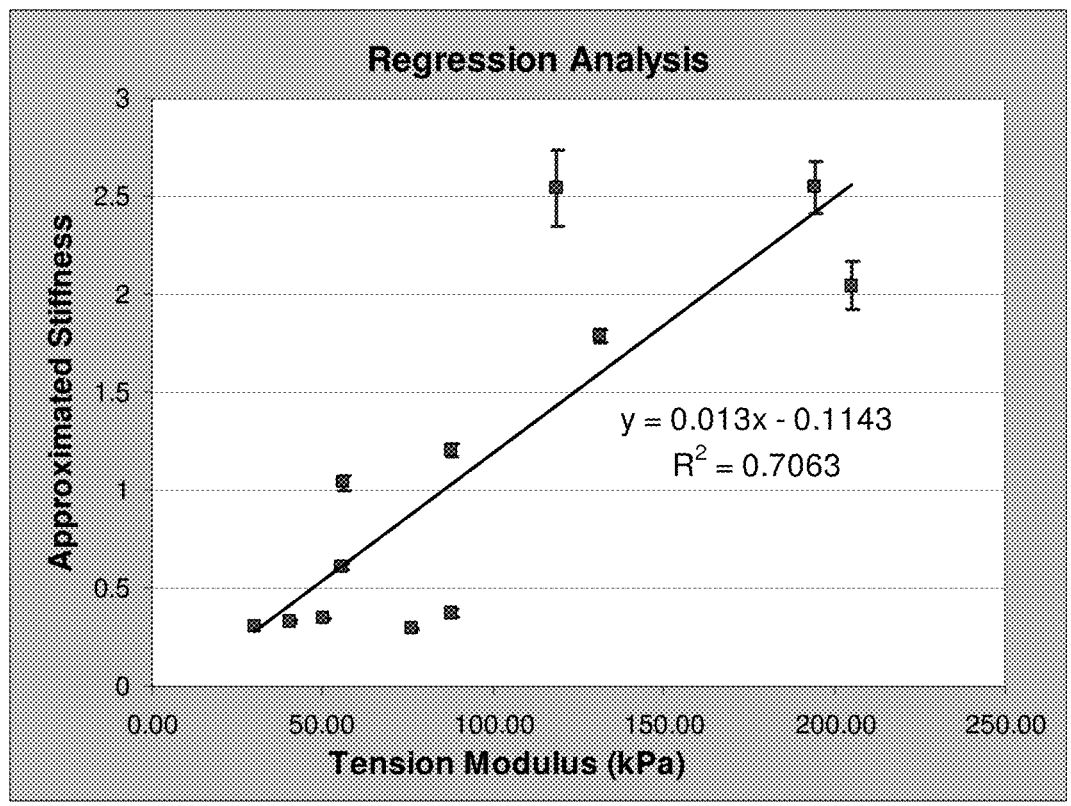
FIG. 10 graphically depicts the relationship between the stiffness findings of tissue interrogation device as compared to reported shear stiffness values.

FIG. 9 illustrates the results of the linear regression analysis for the relationship between the TID's approximate stiffness findings and the liners' reported shear stiffness values. As shown, the analysis yields an $R^2$ value of 0.834, suggesting that about 83% of the total variation in the TID results can be explained by their linear relationship with the reported shear modulus values. FIG. 10 shows the results for the tensile stiffness explanatory variable. This analysis yields an $R^2$ value of 0.706, suggesting a weaker relationship between the TID results and the reported tensile moduli.

Finally, a multiple variable regression was performed to relate the TID results to a combination of both the reported tensile and shear stiffness values:

$$\text{Approximate Stiffness} = 0.016 \times \left(\text{Reported Shear Stiffness}\right) + 7.320 \times 10^{-5} \times \left(\text{Reported Tensile Stiffness}\right) + 0.012 \quad (5)$$

This two-variable analysis yielded an $R^2$ value of 0.834, the same as that obtained for the shear stiffness analysis. Furthermore, a p-value of 0.027 was obtained for the shear stiffness coefficient of the above equation, but for the tensile stiffness coefficient, p=0.989. Therefore, it appears that the shear stiffness values reported by Sanders et al. are useful in explaining the TID's approximated stiffness results, while the tensile stiffness properties are not.

Overall, these results appear to confirm that the prototype skin interrogation device is indeed capable of differentiating materials that have differences in their mechanical properties. Although the device was unable to detect differences between some liners, perhaps this was to be expected. Liners B, C, J, and K are the four products reported by Sanders et al. to compose a low shear stiffness classification of liners, all with shear stiffness properties of approximately 20 kPa. Liner D was reported to have a slightly larger shear modulus value (44 kPa), but shares the same material composition (silicone gel) as the low stiffness group. These five samples are the only liners reported to have this composition. The only other pair of liners that the device failed to differentiate was H and I. These two liners are made by the same manufacturer; they have the same material composition and similar thicknesses; and their shear modulus properties reported by Sanders et al. only show a difference of about 1%.

Table 3 provides a glimpse at the TID's ability to differentiate materials in the presence of environmental and procedural variables that have the potential to affect its output. Unloaded data that were collected coincident with these liner tests suggested that the prototype's output can vary by approximately 2% depending on the ambient conditions. Other device testing revealed an average difference of about 14% when the application force was varied by 0.8N. Also a shift in approach angle by 4° tended to cause approximately 30% difference in the device output. Clearly, in some fashion similar to the methods described herein, future device testing should continue to carefully control these variables so that changes in the TID's output can be confidently attributed to true changes in the properties of the tested materials.

TABLE 3

| Changing Variable | Mean % Difference |
|---|---|
| Temperature Range (69.4° F. to 75.2° F.) | 2.21% |
| 0.8N change in Application Force | 13.58% (0.69 to 31.00) |
| 4° variation in Approach Angle | 30.52% (1.05 to 74.07) |
| Liner Comparisons | 82.45% (0.13 to 158.76) |

Regarding the regression analysis results, they seem to suggest that changes in the output from the prototype device do indeed reflect actual differences in the stiffness properties of tested materials. As shown in FIG. 9, there is a fairly strong linear relationship between the TID output and the reported shear modulus properties of the prosthetic liners. The relationship appears particularly strong for the softer liners, but deviates a bit for the three stiffest samples. Interestingly, these three samples were also the thinnest liners. Perhaps an explanation for the deviation in these results is that, for the thin samples, the boundary condition with the rigid platform of the testing jig may have influenced the results more than with thicker, more compliant liners.

The less than perfect relationship between the TID's output and the reported properties of the tested liners may be further explained by an assumption that was made in the current methodology. The prosthetic liner samples studied herein were assumed to have the same stiffness properties as the liner samples studied four years ago by Sanders et al. However, differences in unknown variables, such as liner shelf-time and manufacturing date, may be present, leading to differences in the samples' characteristics.

As described above, the TID's approximate stiffness results showed a stronger relationship to the liners' reported shear stiffness properties than to their tensile stiffness values. Furthermore, the inclusion of tensile stiffness as a second explanatory variable into the regression analysis provided no further strength to the relationship. Clearly changes in the output of the TID reflect differences in the mechanical stiffness properties of the tested materials. However, if future applications require absolute measurement of intrinsic properties, additional development will be needed to further define the exact relationship between the device output and these intrinsic material properties. It is suspected that the output response from the TID is dependent upon a combination of these properties, and the relative contributions of each may depend on many variables such as the structure of the tested material and the boundary conditions of the testing scenario. For example, the relative homogeneity of the prosthetic liners described herein may have contributed to a stress profile dominated by shear. However, the device may create a different stress profile when applied to human skin. If the morphology of skin is approximated as a thin, relatively stiff layer atop a more fluid-like fatty hypodermis, perhaps the TID's output response would be influenced more by the tensile strain in the superficial layer than by shear strain occurring at the interface with deeper layers.

As the relationship between the TID's output and the intrinsic properties of tissues is further defined, the results presented here seem to predict that the TID will provide an effective tool for detecting changes in the skin. However, the device may have limited ability to detect chronic conditions that begin in deeper tissues. For example, it is generally recognized that static stresses, such as those due to immobility after spinal cord injury, tend to cause pressure ulcers that begin in deeper tissues such as muscle. However, for dynamic stresses such as the high shear loads experienced during ambulation with a prosthesis, the ulceration process often begins in the skin.

Overall, the results the current project have demonstrated the validity of the prototype skin interrogation device as an instrument for measuring the mechanical properties of tested materials. When used to measure the approximate stiffness of different prosthetic liner materials, the device was able to differentiate samples known to have different mechanical properties. Also, the TID's approximate stiffness results for the twelve liners showed strong correlation with their known shear modulus values.

Example 3

Identification of the Spring-Damper Model of the Skin Using the Tissue Interrogation Device Constituent equations of the TID. The constituent equation of the TID could be derived as:

$$F(t) = \frac{2l_1}{3l_s l_2} wh^2 E \epsilon_{diff}(t) \quad (6)$$

Where $\epsilon_{diff}(t)$ is the strain difference between loaded and unloaded trials; w and h are the width and thickness of the piezo layer, respectively; E is the Young's modulus of the bender. $L_1$, $l_2$ and $l_s$ are derived from FIG. 3.

The real deflection during the loaded trials could be derived as:

$$\delta(t) = \frac{(l_1+l_2)l_2^2}{2Ewh^3}F(t) + \frac{3d_{31}(l_1+l_2)l_2}{4h^2}V(t) \quad (7)$$

Where $d_{31}$ is the piezoelectric coefficient, and V(t) is the voltage applied to the bimorph bender in parallel.

Transfer function of simplified skin model. A small patch of skin/tissue could be simplified as a spring and a damper when stretched. The lumped model could be described as:

$$F(t) = d \cdot \frac{dy(t)}{dt} + k \cdot y(t) \quad (8)$$

Where the d is the damper coefficient and k is the spring coefficient. Its description in frequency domain would be:

$$F(s) = dsy(s) + kY(s) \quad (9)$$

Therefore, the transformation is:

$$\frac{Y(s)}{F(s)} = \frac{1}{ds+k} \quad (10)$$

Identification of the skin model. The transfer function of the simplified skin model indicates that the skin acts as a one-pole low pass filter, and its bode plot is exclusively determined by the two parameters d and k. At certain excitation frequency, the system phase lag is:

$$\text{phase of } y(t) - \text{phase of } F(t) = \tan^{-1}\left(\frac{-b\omega}{k}\right) \quad (11)$$

And system gain at the frequency is:

$$\frac{|Y(j\omega)|}{|F(j\omega)|} = \frac{1}{\sqrt{(b\omega)^2 + k^2}} \quad (12)$$

Therefore, by knowing the system gain and phase lag at certain frequency, we could derive the parameters b and k. Alternatively, by applying quasi-static excitation, we could derive k directly from system gain.

Rationale of algorithm for 2 Hz sinusoidal excitation. A 2 Hz sinusoidal wave with 6V amplitude (12V peak-peak) is generated for 5 seconds.

$$V_{control}(t) = 6 \cdot \sin(2*2\pi*t) \quad (13)$$

A voltage is applied to the unloaded TID, and record strain gage output, $\epsilon_{unload}(t)$, is recorded simultaneously. Then, the TIS is loaded on the tissue of interest, a voltage is applied to the TID, and the output of the strain gauge, $\epsilon_{unload}(t)$, is recorded simultaneously. The difference in the output of the loaded and unloaded TID can be determined by:

$$\epsilon_{diff}(t) = \epsilon_{load}(t) - \epsilon_{unload}(t) \quad (14)$$

From this calculation, the force applied to deform the skin can be determined by:

$$F(t) = 0.483 * \epsilon_{diff}(t) \quad (15)$$

The real deformation is determined by:

$$\delta(t) = 6.414 * 10^{-4} * F(t) + 3.041 * 10^{-6} * V(t) \quad (16)$$

where $$V(t) = V_{control}(t) * 2 * \frac{5.6}{1.5} \quad (17)$$

A fast Fourier transform is performed on $F(t)$ to find the magnitude, $|F|_{2Hz}$, and the phase, $\sphericalangle F_{2Hz}$ of $F(t)$ at 2 Hz. Then, a fast Fourier transform on $\delta(t)$ to find the magnitude, $|\delta|_{2Hz}$, and the phase, $\sphericalangle \delta_{2Hz}$ of $\delta(t)$ at 2 Hz. Then, calculate the phase lag as:

$$\sphericalangle \delta_{2Hz} - \sphericalangle F_{2Hz} \quad (18)$$

and calculate $$p = \tan(\sphericalangle \delta_{2Hz} - \sphericalangle F_{2Hz}) \quad (19)$$

The spring coefficient, k, can be calculated as:

$$k = \frac{|F|_{2Hz}}{\sqrt{p^2 + 1}|\delta|_{2Hz}} \quad (20)$$

The damper coefficient, d, can be calculated as:

$$d \frac{p * k}{2 \text{ Hz} * 2\pi} \quad (21)$$

The calculations for $\epsilon_{load}(t)$, $\epsilon_{unload}(t)$, and $V(t)$ can be saved for further modeling. A similar calculation can be performed for 1 Hz and 5 Hz sinusoidal excitation.

Rationale of algorithm for ramp excitation. A five (5) second ramped voltage, $V_{control}$, is generated from $-6V$ to $+6V$ with a 100 Hz sampling rate. A voltage is applied to the unloaded TID, and record strain gage output, $\epsilon_{unload}(t)$, is recorded simultaneously. Then, the TIS is loaded on the tissue of interest, a voltage is applied to the TID, and the output of the strain gauge, $\epsilon_{unload}(t)$, is recorded simultaneously. The difference in the output of the loaded and unloaded TID can be determined by:

$$\epsilon_{diff}(t) = \epsilon_{load}(t) - \epsilon_{unload}(t) \quad (22)$$

From this calculation, the force applied to deform the skin can be determined by:

$$F(t) = 0.483 * \epsilon_{diff}(t) \quad (23)$$

The real deformation is determined by $$\delta(t) = 6.414 * 10^{-4} * F(t) + 3.041 * 10^{-6} * V_{control}(t+6) * 2 * \left(\frac{5.6}{1.5}\right) \quad (24)$$

Then, least square fit the $F(t)$ [y axis] and $\delta(t)$ [x axis], and the slope is k. The calculations for $\epsilon_{load}(t)$, $\epsilon_{unload}(t)$, and $V(t)$ can be saved for further modeling.

Example 3

Zero Order Model for Tissue Interrogation Device

The Tissue Interrogation Device (TID) is capable of detecting subtle changes in mechanical properties of skin and soft tissue. It has a high bandwidth that permits both static and dynamic tissue loading under a wide range of conditions (such as either isotonic or isometric muscle contractions), which make it possible to test for relaxation, creep hysteresis, and stiffness. By recording and analyzing the skins response to mechanical stimulation, it is possible to obtain two of the skin mechanical properties (i.e., elasticity and viscosity).

Instrument design. The TID is comprised of pair of compact, piezoelectric bimorph benders, which apply light mechanical traction to the skin. Large skin strains can be achieved by pulling the skin from two traction surfaces moving in opposite directions. The sensation created by the gauge action is similar to a light vibration and causes no skin irritation, which make it ideal for use with lymphedema patients. A diagram of the device is shown in FIGS. 1 and 2. Two high performance piezo bimorph were mounted on two side print circuit boards (PCBs) to form a pair of tweezers to lead the skin in tension. To measure the relative displacement of the benders, two dual grid strain gages were bonded on the both side of the benders, forming a Wheatstone bridge. The bridge output was processed by a custom-made low distortion amplifier and filtered by a two-pole active low-pass filter with cut-off frequency at 100 Hz. Two high voltage amplifiers were configured in an H-bridge circuit to drive the piezo benders with potential difference between two electrodes varying from −09V to +90V. To eliminate risks of electric shock, two Delrin boots (covered with textured traction pads prevent slipping) were glued on the tip of the piezoelectric benders. In the application of the device a normal force component is necessary to provide the friction grip necessary to load the skin in tension. To reduce the variance of the normal force exerted under manual application, the plastic housing for the unit surrounds the bender tips in such a way as to limit the indentation deformation to less than 1.5 mm.

Preliminary experiments. Preliminary experiments were conducted to validate that the device can reliably discriminate the disparity of biomechanical properties. Literature has shown that biomechanical properties of glabrous skin and hairy skin were quite different. Therefore, a clinically feasible device should be able to consistently distinguish these differences.

The skin responses to a sinusoid signal are demonstrated in FIG. 4. The phase difference between the input and output results from the viscoelastic properties of the skin. For each subject, the shape of the loop of the forearm skin and the palm skin was remarkably different, implying that there were substantial differences in the viscoelastic parameters. In each case, both the slope and the area under the curves could be used as indicators.

In the characterization tests, 12 different commercially available prosthetic liners were used as test materials, the properties of which have been reported in detail by Sanders et al., 2004. Each liner was tested under tightly controlled conditions using the TID and a bench-top positioning device. A one-way ANOVA and subsequent post-hoc tests revealed that the prototype was able to successfully differentiate 55 of 66 (83%) pairs of liner comparisons ($\alpha$=0.05). Linear regression analysis for the relationship between the device output and the liners' reported shear and tensile stiffness properties yielded $R^2$ values of 0.834 and 0.706 respectively. Overall, changes in the measurements from the prototype TID appear to indeed reflect actual changes in the stiffness properties of tested materials. Secondly, the prototype appears capable of differentiating materials that have differences in these properties.

Figure 11:
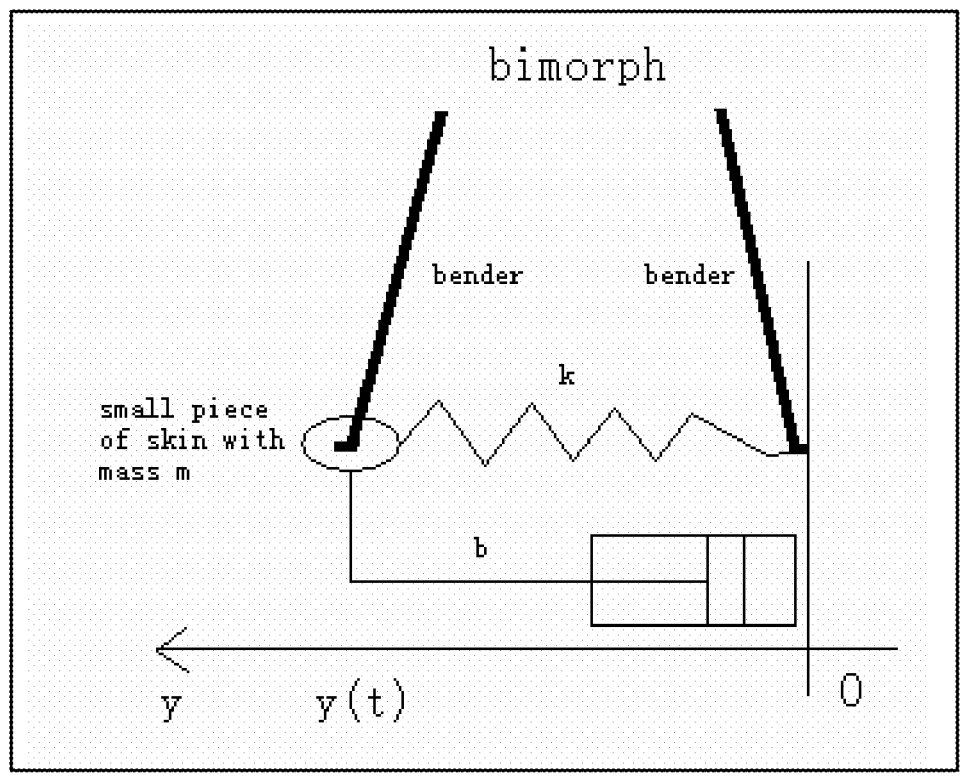
FIG. 11 is a schematic of a small square of skin that is forced to vibrate.

The TID device working process (shown in FIG. 11) can be modeled by a simple one dimensional driven harmonic oscillation with damping.

Suppose the small square is disturbed by a force f to have one dimensional displacement generated. We have f=−ky. Here k is spring constant, which is caused by elasticity. The viscosity of the small square of skin will cause a damping force which is $$f_d = -b\frac{dy}{dt}$$

which is proportional to the speed, where b is the damping coefficient. Simultaneously, the small square of skin is driven by a force $P \sin(\omega t)$. So, one dimensional vibration equation can be written as:

$$m\ddot{y} + b\dot{y} + ky = P \sin(\omega t) \tag{25}$$

For a given small skin area A with thickness h, k and b relates with Young modulus G and viscosity $\eta$ by k=GA/h and b=$\eta$*A/h respectively. So, k and b can be used to describe the skin mechanical properties, i.e. elasticity and viscosity characteristically. From the analysis of forces the small skin area feels, it can be found that whatever one bender is excited to disturb the skin, another bender passively behaves as a sensor or two benders are actively excited to disturb the skin and use strain gage attached with one bender, the equation (1) is always valid in describing the skin dynamics.

The steady vibration solution is:

$$y(t) = \frac{P}{Z\omega}\cos(\omega t - \phi) \text{ where} \tag{26}$$

$$Z = \sqrt{b^2 + \left(\omega m - \frac{k}{m}\right)^2} \text{ and } \phi = \arctan\left(\frac{\omega m - \frac{k}{\omega}}{b}\right)$$

Figure 12:
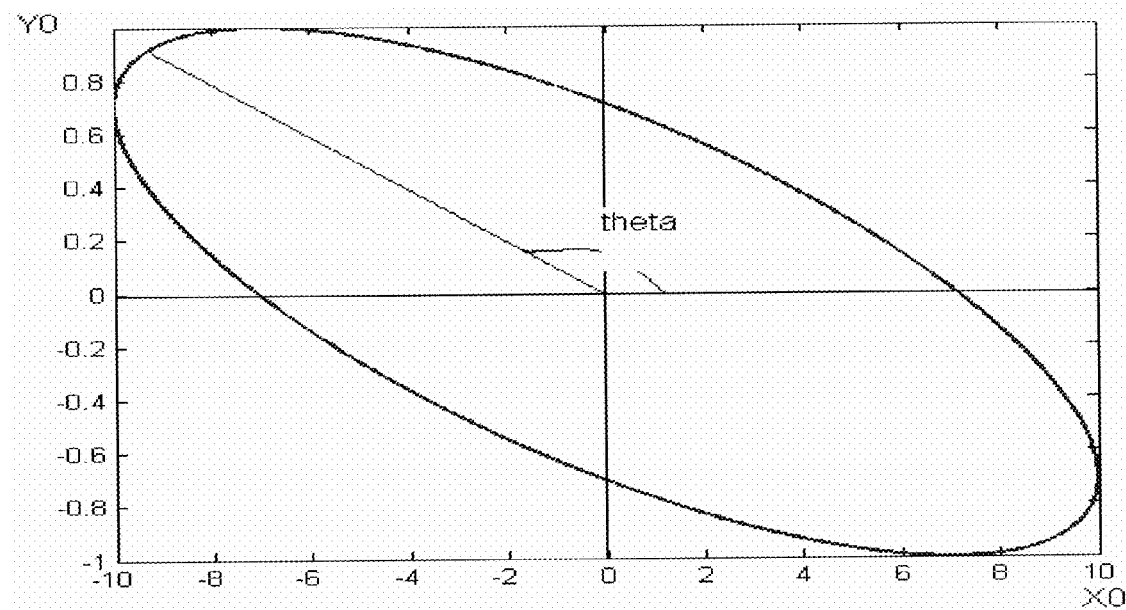
FIG. 12 is a Lissarjous diagram of y(t) and x(t) vibration.

Let $x(t) = P \sin(\omega t)$, then drawing y(t) and x(t) gives a Lissajous diagram which is closed ellipse (FIG. 12). By measuring the amplitude of both variables, we have $$X_0 = 2P \tag{27}$$

$$Y_0 = 2\frac{P}{Z\omega} \tag{28}$$

Then we found:

$$Z = \frac{X_0}{Y_0 \omega} \tag{29}$$

where $\omega$ is known, $\phi$ can be found by $$\sin(\phi) = -\frac{\tan(2\theta)(Z^2\omega^2 - 1)}{2Z\omega} \tag{30}$$

and $\theta$ is the angle of the ellipse (FIG. 12).
Then we solve b and k and get:

$$b = \pm \frac{Z}{\sqrt{1 + \tan(\phi)^2}} \tag{31}$$

$$k \mp \frac{\tan\phi \omega Z}{\sqrt{1 + \tan\phi^2}} + \omega^2 \tag{32}$$

Smith constituent equation.

$$\delta = gf^z + \delta_{free} V/V_{max} \tag{33}$$

$$g = \frac{(l_1 + l_2)l_2^2}{2E\omega h^3} \tag{34}$$

$$\delta_{free} = \frac{3d_{31}(l_1 + l_2)l_2}{4h^2} V_{max} \tag{35}$$

The designed dual pinned bender structure keeps the constituent equation (i.e., Smith equation which expresses the relation among the deflection of bimorph, voltage and external force applied) valid and linear.

$V_{max}$ is maximal voltage applied. E is Young modulus of the ceramic material of the bimorph. $d_{31}$ is the piezoelectric coefficient. h is the thickness of the bimorph $l_1 + l_2$ is the length of the bender. $l_1$ and $l_2$ with two pins make the benders whole length segmented and fixed to be able to make the benders tip reach maximal deflection.

During vibration, the small piece of skin does not feel any other external force except for that generated by the voltage. So, $f_z=0$, and the Smith equation decays to:

$$\delta = \delta_{free}\frac{V}{V_{max}} \tag{36}$$

The physical significance of the equation is voltage V applied can make the bender have the deflection $\delta$. During the process of acquiring data, the voltage applied to the interrogation is always V=90 $\sin(\omega t)$. Thus, deflection is always linear with the change of the voltage.

For a given y as bender's vertical displacement, it will generate voltage v. It is expressed:

$$v(t) = \frac{3h^2 h_{31}}{8l_2(l_1 + l_2)} y(t) = v_{oc} \tag{37}$$

Formula (37) gives the open circuit voltage generated by the bimorph. So, the bender tip's displacement y(t) and the output v(t) only has a constant factor as difference for a given certain bimorph design. As result, drawing output v(t) versus input x(t) as a Lissarjous diagram would also give ellipse which is equivalent to that of y(t) versus x(t) if the interrogation device uses the bender's generated voltage as the output. In present design of the TID, the amplified generated voltage from a strain gage attached with bender is used as output. Since the output can be shown to have the linear relation with the deflection of the bender, the corresponding Lissarjous diagram would be also an ellipse.

So to be able to get the skin mechanical properties k and b, drawing v (t) output and input voltage makes an ellipse as a Lissarjous diagram The force P applied to the forced vibration is shown to have a linear relation with the voltage applied to the bender. By measuring the amplitude (i.e. the lengths of longer and shorter axises) and its inclined angle of the ellipse formula (31) can help to obtain k and b.

Figure 13:
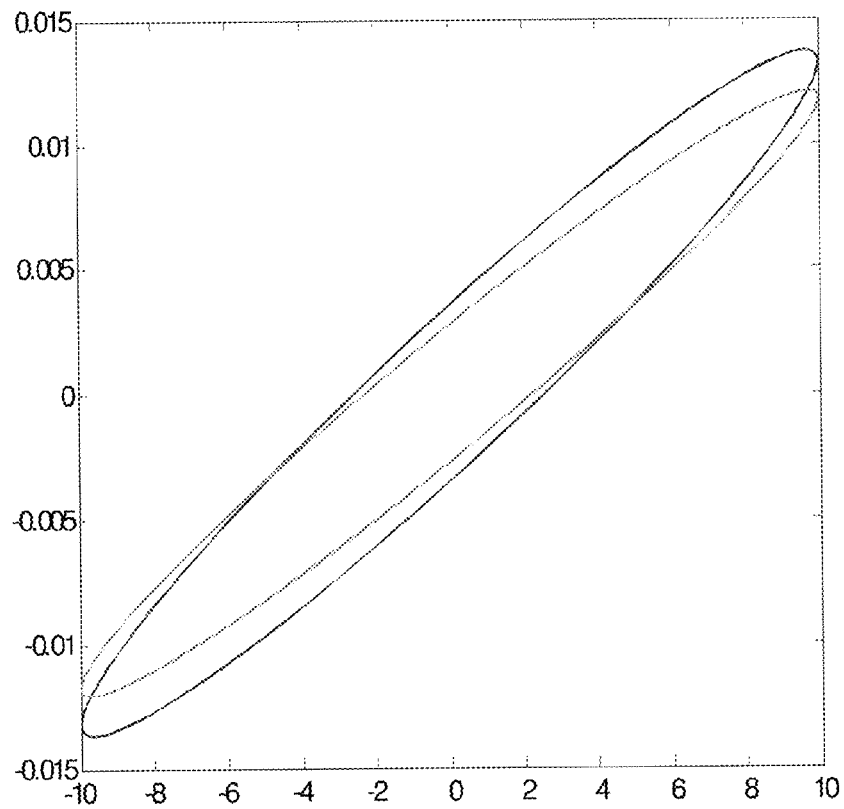
FIG. 13 graphically depicts two ellipses corresponding to three steady state processes with parameter k varying 10%.
Figure 14:
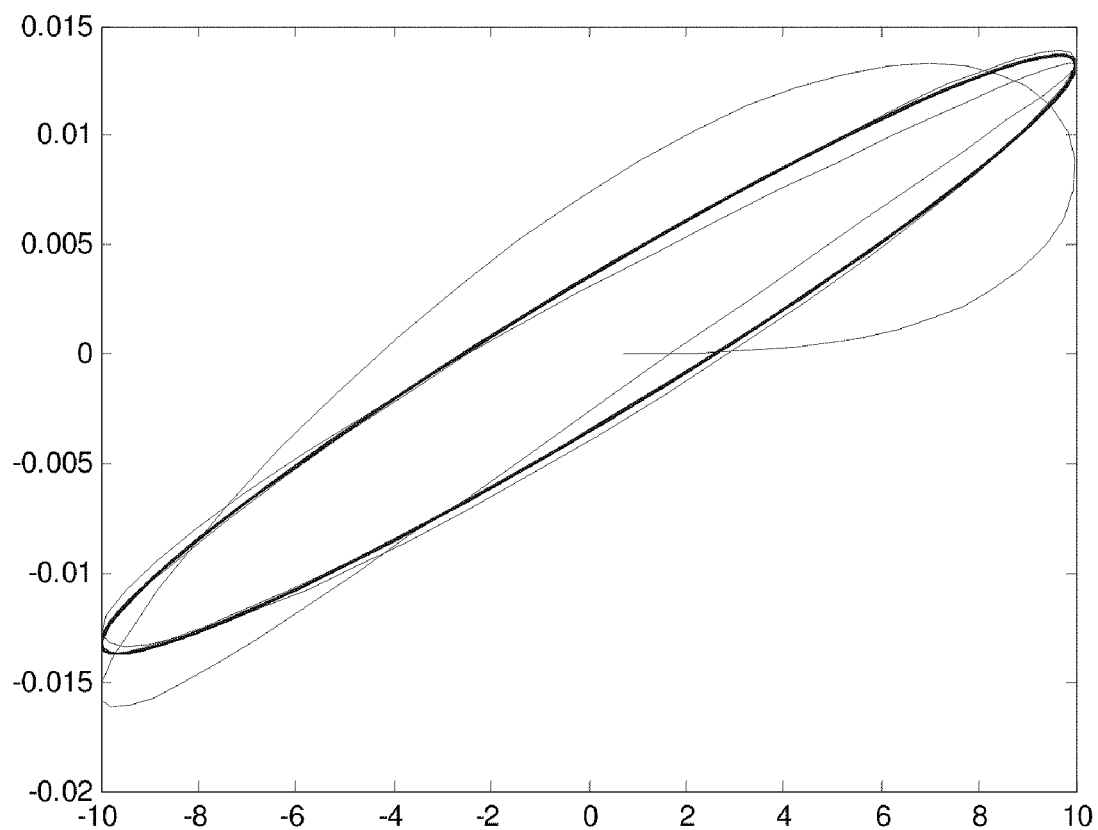
FIG. 14 graphically demonstrate the TID test and the mode output at steady state.

FIG. 13 draws two ellipses correspond to two simulated steady test processes with parameter k varying 10%. FIG. 14 shows a simulated dynamic process of how a steady status is established from a random chosen initial point. These simulation result predicted by the bimorph and skin models agree with the practical observation very well.

Alphabetic Procedure of Calculating the Mechanical Properties of k and b.

(1) For an established measurable steady status, output from skin test should be a very clean and tidy ellipse. Measuring $X_0$ and $Y_0$ (the longer and shorter axises of the ellipse (i.e. the oscillation amplitudes in two different directions)) and inclined angle (2) Calculate Z by $Z = \dfrac{X_0}{Y_0 \omega}$ (3) Calculate $\sin(\phi) = -\dfrac{\tan(2\theta)(Z^2\omega - 1)}{2Z\omega}$ (4) Calculate k and b by equation (31)

During the calculation, the constants or coefficients of some linear relations (e.g., the relation between applied voltage (used to excite bender) and equal force applied) had not been taken into consideration. Not wishing to be bound by any particular theory, it is believed that the difference between different ellipses (e.g. their different inclined angles), not the absolute values of the geometries of an ellipse themselves, are relevant. Thus, comparison of the different values of k and b appears important, for example as expressed in different stages of skin disease. Ignoring these constants and coefficients can help to simply the calculation and the deducted formula.

In clinical application, to be able to determine what quantities are sensitive to the minor mechanical changes, two quantities K(k, b) and B (k, b) can be defined instead of using k and b directly. Preliminary analysis of the solutions (31) and (32) show that, for example K=1000k+100 is really better than k itself. Because minor difference in value K will result in very evident change of the geometries of the ellipse.

Finally, a model which abstracts skin properties from a bimorph in the way described should provide the same conclusion, which is the relation between output and input voltages. The steady output of TID is an ellipse as input (voltage)–output (voltage) diagram (i.e., a Lissarjous diagram). By measuring three parameters of the recorded ellipse, (i.e., the length of its longer axis, the length of its shorter axis, and its inclined angle), a clinician can use the formula to calculate the elasticity and viscosity. Thus, the TID is a dynamic measuring tool of tissue properties, which makes the data processing much easier as compared to other measurement device Quantifying the mechanical responses of tissue experiencing pathological change has potential for use in early detection, differential diagnosis, disease stating, predicting incidence and healing rates and the evaluation of various therapeutic interventions such as pharmacologic agents, compression therapy or pressure reducing support surfaces (e.g., mattresses, seat cushions, shoes, shoe inserts, ad prosthetic sockets, among others). As a clinical tool, the prototype TID and the method of obtaining skin mechanical properties have the potential to replace high risk and/or expensive diagnostic techniques (tissue biopsy and radiological imaging) and improve diagnosis and treatment for any condition in which the tissue is accessible and the pathology is manifested in the mechanical properties of the tissue. To be able to reach the purpose, the embryonic prototype Tissue Interrogation Device (TID) will be validated by testing its clinical utility in a study of fibrosis in individuals with lymphedema. The TID will be used to characterize the mechanical properties of both normal and lymphatic tissue. Mechanical tissue properties will represent a clinical construct of tissue fibrosis. Data collection will be developed and promoted in the area where the skin disease occurs and transverses much more serious. Data analysis will be proceeded to discriminate between normal tissue and disease tissue.

Clinical validation process will also suggest how the device should be improved. The re-engineered device will be a potential candidate which is low cost. It will be suitable for use in home-based healthcare. In particular the billions of patients suffering worldwide with venous disease, lymphedema, diabetic foot disease and scleroderma, especially in those poor economic and medicine lack areas would benefit tremendously from the inexpensive, hand-held clinical tool to clarify and advance the understanding of potential etiologic factors, the pathogenesis of these diseases, and current treatment. In addition, reengineered TID (Tissue Interrogation Device) can be potential new self-care technique and device. On the other hand, the device also offers the chance of many other potential applications, for example simply and fast sorting and monitoring the polymers with different mechanical properties in industry.

The relation between driving voltage and the generated force. The relation between driving voltage V and force supposed P is also linear.

To be able to show this conclusion, combining Equations (26) and (36) can make get relation between driving voltage V and force supposed P:

$$V(t) = C\dfrac{P}{Z\omega}\cos(\omega t - \phi) \qquad (38)$$

The quantities Z, P and $\phi$ are the same as what previously defined.

So, for a given vibration frequency w the ratio between modes of the applied driving force and voltage, or $$\dfrac{|V|}{|P|} \text{ is constant} \qquad (39)$$

Equation (18) had been approved theoretically and experimentally as correct relation for unimorphs and multimorphs by many works published in the past decade.

What is claimed is:

1. A system for deriving at least one mechanical property of a skin and tissue, the system comprising:
   (a) an excitation generator configured to generate a predetermined excitation at a predetermined time;
   (b) a first elongated member having a first distal end configured to contact the skin at a first position;
   (c) a second elongated member that has a second distal end configured to contact the skin at a second position spaced apart from the first position, the second elongated member including a flexion element that is constrained in two different spaced apart places and that is configured to apply a first strain tangentially to the skin in a first direction in response to the predetermined excitation;
   (d) a detection element configured to measure a parameter of the first flexion element in response to the predetermined excitation; and
   (e) a processing system to calculate the at least one mechanical property of the skin and tissue based on the parameter measured by the detection element.

2. The system of claim 1, wherein the mechanical property is selected from a list of properties consisting of: elasticity, viscosity, surface stiffness, surface thickness, relaxation, creep, hysteresis, and combinations thereof.

3. The system of claim 1, wherein the excitation generator comprises an electronic circuit configured to generate an electrical excitation.

4. The system of claim 1, wherein the flexion element comprises:
   (a) a metal strip; and
   (b) a piezoelectric strip affixed to the metal strip and configured to change length in response to an electrical excitation.

5. The system of claim 1, wherein the first elongated member comprises a flexion element that is constrained in two different spaced apart places and that is configured to apply a force tangentially to the skin in a second direction, different from the first direction, in response to the excitation.

6. The system of claim 5, wherein the flexion element comprises:
   (a) a metal strip; and
   (b) a piezoelectric strip affixed to the metal strip and configured to change length in response to an electrical excitation.

7. The system of claim 1, further comprising a first set of pins that is configured to constrain the flexion element in a first place and a second set of pins spaced apart at a distance from the first set of pins and that is configured to constrain the flexion element in a second place, different from the first place.

8. The system of claim 7, wherein at least one of the first set of pins and the second set of pins is adjustable so as to be configured to adjust the distance between the first place and the second place.

9. The system of claim 7, further comprising a pair insulating elements disposed on the first elongated member and the second elongated member so as to electrically isolate the first elongated member and the second elongated member from the skin.

10. A method for measuring a mechanical property of a surface, comprising the steps of:
    (a) placing a first elongated member against the surface;
    (b) applying an excitation to a first flexion element, a portion of which is in contact with the surface at a position that is spaced apart from the first elongated member, thereby causing the first flexion element to apply a strain tangentially to the surface;
    (c) measuring a deflection of the first flexion element when the excitation is being applied thereto; and
    (d) calculating, using a digital processor, the mechanical property of the surface based on the strain and the deflection.

11. The method of claim 10, wherein the mechanical property is selected from a list of mechanical properties consisting of: elasticity, viscosity, surface stiffness surface thickness, relaxation, creep, hysteresis, and combinations thereof.

12. The method of claim 10, wherein the surface comprises a skin.

13. The method of claim 10, wherein the excitation comprises an electrical excitation.

14. The method of claim 10, wherein the flexion element comprises:
    (a) a metal strip; and
    (b) a piezoelectric strip affixed to the metal strip, and
    wherein the excitation comprise and electrical excitation applied to the piezoelectric strip thereby causing the piezoelectric strip to change in length.

15. The method of claim 10, further comprising the step of constraining the first flexion element in two spaced apart places.

16. The method of claim 10, wherein the first elongated member comprises a flexion element, the method further comprising the step of applying an excitation to the first elongated element.

* * * * *